(12) United States Patent
Thomas et al.

(10) Patent No.: US 6,184,028 B1
(45) Date of Patent: Feb. 6, 2001

(54) POLYPEPTIDES HAVING PECTIN ACETYLESTERASE ACTIVITY AND NUCLEIC ACIDS ENCODING SAME

(75) Inventors: Michael D. Thomas, Davis; Kimberly M. Brown, Elk Grove, both of CA (US)

(73) Assignee: Novo Nordisk Biotech, Inc., Davis, CA (US)

( * ) Notice: Under 35 U.S.C. 154(b), the term of this patent shall be extended for 0 days.

(21) Appl. No.: 09/384,305

(22) Filed: Aug. 26, 1999

(51) Int. Cl.[7] ..................................................... C08B 30/04
(52) U.S. Cl. ........................ 435/275; 435/196; 435/71.1
(58) Field of Search .................................. 435/196, 71.1, 435/275

(56) References Cited

FOREIGN PATENT DOCUMENTS

WO 93/20190    10/1993   (DK) .

OTHER PUBLICATIONS

Yoshida et al. Sequencing of a 65 kb region of the *Bacillus subtilis* genome containing the lic and cel loci, and creation of a 177 kb contig covering the gnt–sacXY region. Microbiology (1996) 142, 3113–3123, Nov. 1996.*

Kunst et al. The complete genome sequence of the gram-positive bacterium *Bacillus subtilis*. Nature (1997) 390 (6657): 249–256, Nov. 1997.*

Shevchik et al., 1997, Molecular Microbiology 24: 1285–1301.

Breton et al., 1996, FEBS Letters 388: 139–142.

Kauppinen et al., 1995, Journal of Biological Chemistry 270: 27172–27178.

* cited by examiner

*Primary Examiner*—Ponnathapu Achutamurthy
*Assistant Examiner*—Kathleen Kerr
(74) *Attorney, Agent, or Firm*—Robert Starnes; Elias Lambiris, Esq.

(57) ABSTRACT

The present invention relates to isolated polypeptides having pectin acetylesterase activity and isolated nucleic acid sequences encoding the polypeptides. The invention also relates to nucleic acid constructs, vectors, and host cells comprising the nucleic acid sequences as well as methods for producing and using the polypeptides.

7 Claims, 12 Drawing Sheets

ATGAAAAATGGATGGCAGCGGGTTTTTGTGATGATGCTGATGTGTTTTGGCGGGATTGAGAATGTGA 70
 M  K  W  M  A  A  V  F  V  M  M  L  M  L  C  F  G  G  I  E  N  V
AGGCGGCGGAGCCGAAGGTGTATCAGTTTGACTTTGGAAGCGGTTCGATGGAGCCTGGTTATATTGGTGT 140
 K  A  A  E  P  K  V  Y  Q  F  D  F  G  S  G  S  M  E  P  G  Y  I  G  V
CAGGGCGTCTGATCGGTATGACCGGTCAAAGGGCTGTTTCAGTTTTTAGCGTATGGGACGAAAAGCAATAACA 210
 R  A  S  D  R  Y  D  R  S  K  G  Y  G  F  Q  T  P  E  N  M  R  D  V
GCGGCATCCGGGGCTGGTGTGAAGAGTGATGGCCTTTATGAGGTGAAGTGACGCTTGCAATACGGCAAGGCCAG 280
 A  A  S  G  A  G  V  K  S  D  A  V  Q  F  L  A  Y  G  T  K  S  N  N
CGTTTAATGTTGATCTCCCGAATGGCCTTTATGAGGTGAAGTGACGCTTGCAATACGGCAAGGCCAG 350
 T  F  N  V  D  L  P  N  G  L  Y  E  V  K  V  T  L  G  N  T  A  R  A  S
TGTGGCAGCGGAGGGCGTGTTTCAGGTCATCAATATGACAGGGGATGCGCGGAGATACGTTCCAAATT 420
 V  A  A  E  G  V  F  Q  V  I  N  M  T  G  D  G  A  E  D  T  F  Q  I
CCCGTCACCGACGGGCAGCTGAATCTCCTGGTGACAGAGGGAAAGCAGGCACCGCTTTTACGCTCAGCG 490
 P  V  T  D  G  Q  L  N  L  L  V  T  E  G  K  A  G  T  A  F  T  L  S
CCTTGAAAATAAGAAATTGTCTGATCAGCCGGTAACGAATCGAACCATTTATGTCGGGGACTCGAC 560
 A  L  K  I  K  K  L  S  D  Q  P  V  T  N  R  T  I  Y  V  G  G  D  S  T
GGTGTGCAATTATTATCCGCTCAACAGCAGCAAGCAGGCGGGCCAGATGCTGCCTCACTATATC 630
 V  C  N  Y  Y  P  L  N  S  S  K  Q  A  G  W  G  Q  M  L  P  H  Y  I
GATAAACACACCTTTCAAGTGAGAAACATGGCGTCTGGCGGGCAGATTATTTTATGTTGCAGCTTGGCATTAATGA 700
 D  K  H  T  F  Q  V  R  N  M  A  S  G  G  Q  I  A  R  G  F  R  N  D
GACAGCTTGAGGCGATTCTGAAGTATATTAAAACCGGAGTTTAAAGAGGTGATGCTGATATGATTCGTCAGGTA 770
 Q  L  E  A  I  L  K  Y  I  K  P  G  D  Y  F  M  L  Q  L  G  I  N  D
CACAAAATCCGAAGCATAAAGAATCTGAAGCGGAGTTTAAAGAGGTGATGCTGATATGATTCGTCAGGTA 840
 T  N  P  K  H  K  E  S  E  A  E  F  K  E  V  M  R  D  M  I  R  Q  V
AAAGCGAAAGGAGCGGACGTCATCTCTACAGGGCAAACCGATTTTACTTCTGAAGGCA 910
 K  A  K  G  A  D  V  I  L  S  T  P  Q  G  R  A  T  D  F  T  S  E  G
TCCATTCGTCTGTAAACAGATGGTACAGGGCCTCTATTTAGCTTTGGCCGAAGAGGAAAAAACATATCT 980
 I  H  S  S  V  N  R  W  Y  R  A  S  I  L  A  L  A  E  E  K  T  Y  L
CATTGACTTAAATGTCCTCAGCTCGGCATACTTTACATCGATCGGTCCGGAAAGAACACTCGGCTTTAT 1050
 I  D  L  N  V  L  S  S  A  Y  F  T  S  I  G  P  E  R  T  L  G  L  Y
ATGGATGGAGATACGCTGCACCCGAATCGCGGGGGCCACTGGCGCGATTGGCGTGTTCAGGAGC 1120
 M  D  G  D  T  L  H  P  N  R  A  G  A  D  A  L  A  R  L  A  V  Q  E
TAAAACGCCAGGGAATCGCTGGCTTTTAA 1149
 L  K  R  Q  G  I  A  G  F  .

Fig. 1

```
                    SfiI
              GGCCT TAAGGGCCTG CAATCGATTG TTTGAGAAAA

GAAGAAGACC ATAAAAATAC CTTGTCTGTC ATCAGACAGG GTATTTTTA

-35
                                       t                   a
TGCTGTCCAG ACTGTCCGCT GTGTAAAAAA AAGGAATAAA GGGGGGTTGT

-10
c                   t                                 SacI
TATTATTTTA CTGATATGTA AAATATAATT TGTATAAGAA AATGGAGCTC
```

POLYPEPTIDES HAVING PECTIN ACETYLESTERASE ACTIVITY AND NUCLEIC ACIDS ENCODING SAME

BACKGROUND OF THE INVENTION

1. Field of the Invention

The present invention relates to isolated polypeptides having pectin acetylesterase activity and isolated nucleic acid sequences encoding the polypeptides. The invention also relates to nucleic acid constructs, vectors, and host cells comprising the nucleic acid sequences as well as methods for producing and using the polypeptides.

2. Description of the Related Art

Pectins are important structural components of plant cell walls. The main backbone in pectins can be divided into linear homogalacturonan (smooth) regions of up to 200 residues of 1,4-linked α-D-galacturonic acid (GalUA) and highly branched rhamnogalacturonan (hairy) regions consisting of repeating α-(1,2)-L-rhamnose-α-(4)-D-galacturonic acid disaccharide units. In general, about half of the rhamnose residues are substituted with neutral oligosaccharides such as arabinans, galactans, and arabinogalactans. Most pectic substances are also esterified at some of the α-D-galacturonic acid residues with methyl at the carboxyl group or acetyl at the hydroxyl groups at the C-2 and/or C-3 positions.

Pectin acetylesterase catalyzes the deacetylation of the acetyl groups at the hydroxyl groups of the linear homogalacturonan (smooth) regions. Rhamnogalacturonan acetylesterase catalyzes the deacetylation of the acetyl groups at the hydroxyl groups of the highly branched rhamnogalacturonan (hairy) regions.

Pectin acetylesterases have been isolated from *Erwinia chrysanthemi* (Shevchik et al., 1997, *Molecular Microbiology* 24: 1285–1301); *Vigna radiata* L (Breton et al., 1996, *FEBS Letters* 388: 139–142); and *Aspergillus niger* (Searle-Van Leeuwen et al., 1996, *Progress in Biotechnology* pp. 793–798).

A rhamnogalacturonan acetylesterase has been isolated from *Aspergillus aculeatus* (Kauppinen et al., 1995, *Journal of Biological Chemistry* 270: 27172–27178; WO 93/20190).

A gene encoding pectin acetylesterase has been isolated from *Erwinia chrysanthemi* (Shevchik et al., 1997, supra).

A gene encoding rhamnogalacturonan acetylesterase has been isolated from *Aspergillus aculeatus* (Kauppinen et al., 1995, supra).

It is an object of the present invention to provide improved polypeptides having pectin acetylesterase activity and nucleic acids encoding the polypeptides.

SUMMARY OF THE INVENTION

The present invention relates to isolated polypeptides having pectin acetylesterase activity selected from the group consisting of:

(a) a polypeptide having an amino acid sequence which has at least 65% identity with amino acids 26 to 382 of SEQ ID NO:2;

(b) a polypeptide encoded by a nucleic acid sequence which hybridizes under low stringency conditions with (i) nucleotides 76 to 1146 of SEQ ID NO:1, (ii) a subsequence of (i) of at least 100 nucleotides, or (iii) a complementary strand of (i) or (ii);

(c) a variant of the polypeptide having an amino acid sequence of SEQ ID NO:2 comprising a substitution, deletion, and/or insertion of one or more amino acids;

(d) an allelic variant of (a) or (b); and (e) a fragment of (a), (b), or (d) that has pectin acetylesterase activity.

The present invention also relates to isolated nucleic acid sequences encoding the polypeptides and to nucleic acid constructs, vectors, and host cells comprising the nucleic acid sequences as well as methods for producing and using the polypeptides.

BRIEF DESCRIPTION OF THE FIGURES

FIG. 1 shows the genomic DNA sequence and the deduced amino acid sequence of a *Bacillus subtilis* 168 pectin acetylesterase (SEQ ID NOS:1 and 2, respectively).

FIG. 9 shows a nucleic acid sequence containing the "consensus" amyQ promoter (SEQ ID NO:20).

DETAILED DESCRIPTION OF THE INVENTION

Polypeptides Having Pectin Acetylesterase Activity

Figure 2:
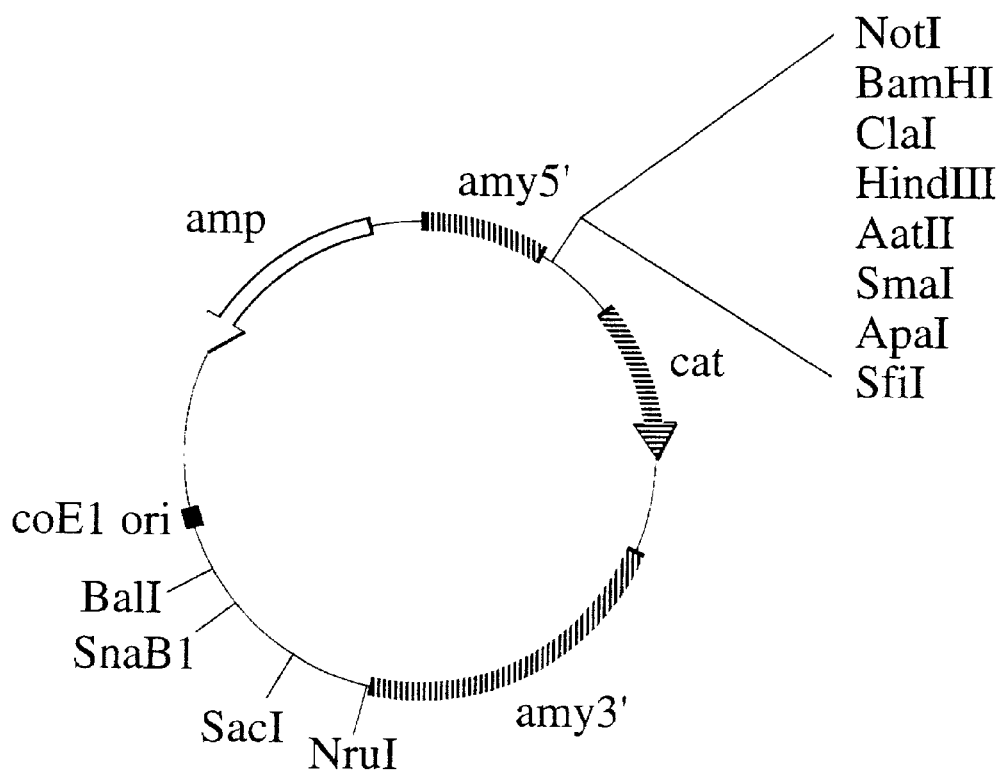
FIG. 2 show shows a restriction map of pDG268MCS.

The term "pectin acetylesterase activity" is defined herein as an acetyl esterase activity which catalyzes the deacetylation of the acetyl groups at the hydroxyl groups of GalUA residues of pectin. For purposes of the present invention, pectin acetylesterase activity is determined using p-nitrophenylacetate as substrate where 4.5 mM p-nitrophenylacetate in 100 mM MOPS-4 mM calcium chloride pH 7.5 is incubated with the acetylesterase at 25° C. and the amount of released p-nitrophenolate ion is measured as a function of time at 405 nM. One unit of pectin acetylesterase activity is defined as 1.0 μmole of p-nitrophenolate ion produced from p-nitrophenylacetate per minute at 25° C., pH 7.5.

In a first embodiment, the present invention relates to isolated polypeptides having an amino acid sequence which has a degree of identity to amino acids 26 to 382 of SEQ ID NO:2 (i.e., the mature polypeptide) of at least about 65%, preferably at least about 70%, more preferably at least about 80%, even more preferably at least about 90%, most preferably at least about 95%, and even most preferably at least about 97%, which have pectin acetylesterase activity (hereinafter "homologous polypeptides"). In a preferred embodiment, the homologous polypeptides have an amino acid sequence which differs by five amino acids, preferably by four amino acids, more preferably by three amino acids, even more preferably by two amino acids, and most preferably by one amino acid from amino acids 26 to 382 of SEQ ID NO:2. For purposes of the present invention, the degree of identity between two amino acid sequences is determined by the Clustal method (Higgins, 1989, *CABIOS* 5: 151–153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5.

Preferably, the polypeptides of the present invention comprise the amino acid sequence of SEQ ID NO:2 or an allelic variant thereof; or a fragment thereof that has pectin acetylesterase activity. In a more preferred embodiment, the polypeptide of the present invention comprises the amino acid sequence of SEQ ID NO:2. In another preferred embodiment, the polypeptide of the present invention comprises amino acids 26 to 382 of SEQ ID NO:2, or an allelic variant thereof, or a fragment thereof that has pectin acetylesterase activity. In another preferred embodiment, the polypeptide of the present invention comprises amino acids 26 to 382 of SEQ ID NO:2. In another preferred embodiment, the polypeptide of the present invention consists of the amino acid sequence of SEQ ID NO:2 or an allelic variant thereof; or a fragment thereof that has pectin acetylesterase activity. In another preferred embodiment, the polypeptide of the present invention consists of the amino acid sequence of SEQ ID NO:2. In another preferred embodiment, the polypeptide consists of amino acids 26 to 382 of SEQ ID NO:2 or an allelic variant thereof; or a fragment thereof that has pectin acetylesterase activity. In another preferred embodiment, the polypeptide consists of amino acids 26 to 382 of SEQ ID NO:2.

A fragment of SEQ ID NO:2 is a polypeptide having one or more amino acids deleted from the amino and/or carboxyl terminus of this amino acid sequence. Preferably, a fragment contains at least 310 amino acid residues, more preferably at least 325 amino acid residues, and most preferably at least 350 amino acid residues.

An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

In a second embodiment, the present invention relates to isolated polypeptides having pectin acetylesterase activity which are encoded by nucleic acid sequences which hybridize under very low stringency conditions, preferably low stringency conditions, more preferably medium stringency conditions, more preferably medium-high stringency conditions, even more preferably high stringency conditions, and most preferably very high stringency conditions with a nucleic acid probe which hybridizes under the same conditions with (i) nucleotides 76 to 1146 of SEQ ID NO:1, (ii) a subsequence of (i), or (iii) a complementary strand of (i) or (ii) (J. Sambrook, E. F. Fritsch, and T. Maniatus, 1989, *Molecular Cloning, A Laboratory Manual*, 2d edition, Cold Spring Harbor, N.Y.). The subsequence of SEQ ID NO:1 may be at least 100 nucleotides or preferably at least 200 nucleotides. Moreover, the subsequence may encode a polypeptide fragment which has pectin acetylesterase activity. The polypeptides may also be allelic variants or fragments of the polypeptides that have pectin acetylesterase activity.

The nucleic acid sequence of SEQ ID NO:1 or a subsequence thereof, as well as the amino acid sequence of SEQ ID NO:2 or a fragment thereof, may be used to design a nucleic acid probe to identify and clone DNA encoding polypeptides having pectin acetylesterase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Longer probes can also be used. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

Thus, a genomic DNA library prepared from such other organisms may be screened for DNA which hybridizes with the probes described above and which encodes a polypeptide having pectin acetylesterase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO:1 or a subsequence thereof, the carrier material is used in a Southern blot. For purposes of the present invention, hybridization indicates that the nucleic acid sequence hybridizes to a labeled nucleic acid probe corresponding to the nucleic acid sequence shown in SEQ ID NO:1, its complementary strand, or a subsequence thereof, under very low to very high stringency conditions. Molecules to which the nucleic acid probe hybridizes under these conditions are detected using X-ray film.

In a preferred embodiment, the nucleic acid probe is a nucleic acid sequence which encodes the polypeptide of SEQ ID NO:2, or a subsequence thereof. In another preferred embodiment, the nucleic acid probe is SEQ ID NO:1. In another preferred embodiment, the nucleic acid probe is the mature polypeptide coding region of SEQ ID NO:1. In another preferred embodiment, the nucleic acid probe is the nucleic acid sequence contained in plasmid pCR2.1-yxiM which is contained in *Escherichia coli* NRRL B-30151, wherein the nucleic acid sequence encodes a polypeptide having pectin acetylesterase activity. In another preferred embodiment, the nucleic acid probe is the mature polypeptide coding region of the nucleic acid sequence contained in plasmid pCR2.1-yxiM which is contained in *Escherichia coli* NRRL B-30151, which encodes a polypeptide having pectin acetylesterase activity.

For long probes of at least 100 nucleotides in length, very low to very high stringency conditions are defined as prehybridization and hybridization at 42° C. in 5×SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures.

For long probes of at least 100 nucleotides in length, the carrier material is finally washed three times each for 15 minutes using 2×SSC, 0.2% SDS preferably at least at 45° C. (very low stringency), more preferably at least at 50° C.(low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third embodiment, the present invention relates to variants of the polypeptide having an amino acid sequence of SEQ ID NO:2 comprising a substitution, deletion, and/or insertion of one or more amino acids.

The amino acid sequences of the variant polypeptides may differ from the amino acid sequence of SEQ ID NO:2 or the mature polypeptide thereof by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20–25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, *In, The Proteins,* Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

In a fourth embodiment, the present invention relates to isolated polypeptides having immunochemical identity or partial immunochemical identity to the polypeptide having the amino acid sequence of SEQ ID NO:2 or the mature polypeptide thereof. The immunochemical properties are determined by immunological cross-reaction identity tests by the well-known Ouchterlony double immunodiffusion procedure. Specifically, an antiserum containing polyclonal antibodies which are immunoreactive or bind to epitopes of the polypeptide having the amino acid sequence of SEQ ID NO:2 or the mature polypeptide thereof are prepared by immunizing rabbits (or other rodents) according to the procedure described by Harboe and Ingild, In N. H. Axelsen, J. Kroll, and B. Weeks, editors, *A Manual of Quantitative Immunoelectrophoresis,* Blackwell Scientific Publications, 1973, Chapter 23, or Johnstone and Thorpe, *Immunochemistry in Practice,* Blackwell Scientific Publications, 1982 (more specifically pages 27–31). A polypeptide having immunochemical identity is a polypeptide which reacts with the antiserum in an identical fashion such as total fusion of precipitates, identical precipitate morphology, and/or identical electrophoretic mobility using a specific immunochemical technique. A further explanation of immunochemical identity is described by Axelsen, Bock, and Kroll, In N. H. Axelsen, J. Kroll, and B. Weeks, editors, *A Manual of Quantitative Immunoelectrophoresis,* Blackwell Scientific Publications, 1973, Chapter 10. A polypeptide having partial immunochemical identity is a polypeptide which reacts with the antiserum in a partially identical fashion such as partial fusion of precipitates, partially identical precipitate morphology, and/or partially identical electrophoretic mobility using a specific immunochemical technique. A further explanation of partial immunochemical identity is described by Bock and Axelsen, In N. H. Axelsen, J. Kroll, and B. Weeks, editors, *A Manual of Quantitative Immunoelectrophoresis,* Blackwell Scientific Publications, 1973, Chapter 11.

The antibody may also be a monoclonal antibody. Monoclonal antibodies may be prepared and used, e.g., according to the methods of E. Harlow and D. Lane, editors, 1988, *Antibodies, A Laboratory Manual,* Cold Spring Harbor Press, Cold Spring Harbor, N.Y.

The polypeptides of the present invention have at least 20%, preferably at least 40%, more preferably at least 60%, even more preferably at least 80%, even more preferably at least 90%, and most preferably at least 100% of the pectin acetylesterase activity of the mature polypeptide of SEQ ID NO:2.

A polypeptide of the present invention may be obtained from microorganisms of any genus. For purposes of the present invention, the term "obtained from" as used herein in connection with a given source shall mean that the polypeptide encoded by the nucleic acid sequence is produced by the source or by a cell in which the nucleic acid sequence from the source has been inserted. In a preferred embodiment, the polypeptide is secreted extracellularly.

A polypeptide of the present invention may be a bacterial polypeptide. For example, the polypeptide may be a gram positive bacterial polypeptide such as a Bacillus polypeptide, or a Streptomyces polypeptide, e.g., a *Streptomyces lividans* or *Streptomyces murinus* polypeptide; or a gram negative bacterial polypeptide, e.g., an *E. coli* or a Pseudomonas sp. polypeptide.

In a preferred embodiment, a polypeptide of the present invention is obtained from a strain of the genus Bacillus, as defined by Fergus G. Priest In Abraham I,. Sonenshein, James A. Hoch, and Richard Losick, editors, *Bacillus subtilis and Other Gram-Positive Bacteria,* American Society For Microbiology, Washington, D.C., 1993, pages 3–16.

In a more preferred embodiment, the polypeptide is obtained from a *Bacillus alkalophilus, Bacillus amyloliquefaciens, Bacillus brevis, Bacillus circulans, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* strain.

In a most preferred embodiment, the polypeptide is a *Bacillus subtilis* polypeptide, and most preferably a *Bacillus subtilis* 168 polypeptide, e.g., the polypeptide with the amino acid sequence of SEQ ID NO:2.

Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a genomic or cDNA library of another microorganism. Once a nucleic acid sequence encoding a polypeptide has been detected with the probe(s), the sequence may be isolated or cloned by utilizing techniques which are known to those of ordinary skill in the art (see, e.g., Sambrook et al., 1989, supra).

As defined herein, an "isolated" polypeptide is a polypeptide which is essentially free of other non-pectin acetylesterase polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE.

Polypeptides encoded by nucleic acid sequences of the present invention also include fused polypeptides or cleavable fusion polypeptides in which another polypeptide is fused at the N-terminus or the C-terminus of the polypeptide or fragment thereof. A fused polypeptide is produced by fusing a nucleic acid sequence (or a portion thereof) encoding another polypeptide to a nucleic acid sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Nucleic Acid Sequences

The present invention also relates to isolated nucleic acid sequences which encode a polypeptide of the present invention. In a preferred embodiment, the nucleic acid sequence is set forth in SEQ ID NO:1. In another more preferred embodiment, the nucleic acid sequence is the sequence contained in plasmid pCR2.1-yxiM that is contained in *Escherichia coli* NRRL B-30151. In another preferred embodiment, the nucleic acid sequence is the mature polypeptide coding region of SEQ ID NO:1. In another more preferred embodiment, the nucleic acid sequence is the mature polypeptide coding region contained in plasmid pCR2.1-yxiM that is contained in *Escherichia coli* NRRL B-30151. The present invention also encompasses nucleic acid sequences which encode a polypeptide having the amino acid sequence of SEQ ID NO:2 or the mature polypeptide thereof, which differ from SEQ ID NO:1 by virtue of the degeneracy of the genetic code. The present invention also relates to subsequences of SEQ ID NO:1 which encode polypeptide fragments of SEQ ID NO:2 that have pectin acetylesterase activity.

A subsequence of SEQ ID NO:1 is a nucleic acid sequence encompassed by SEQ ID NO:1 except that one or more nucleotides from the 5' and/or 3' end have been deleted. Preferably, a subsequence contains at least 930 nucleotides, more preferably at least 975 nucleotides, and most preferably at least 1050 nucleotides.

The present invention also relates to mutant nucleic acid sequences comprising at least one mutation in the mature polypeptide coding sequence of SEQ ID NO:1, in which the mutant nucleic acid sequence encodes a polypeptide which consists of amino acids 26 to 382 of SEQ ID NO:2.

The techniques used to isolate or clone a nucleic acid sequence encoding a polypeptide are known in the art and include isolation from genomic DNA, preparation from cDNA, or a combination thereof. The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application,* Academic Press, New York. Other nucleic acid amplification procedures such as ligase chain reaction (LCR), ligated activated transcription (LAT) and nucleic acid sequence-based amplification (NASBA) may be used. The nucleic acid sequence may be cloned from a strain of Bacillus, or another or related organism and thus, for example, may be an allelic or species variant of the polypeptide encoding region of the nucleic acid sequence.

The term "isolated nucleic acid sequence" as used herein refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

The present invention also relates to nucleic acid sequences which have a degree of homology to the mature polypeptide coding sequence of SEQ ID NO:1 (i.e., nucleotides 76 to 1146) of at least about 65%, preferably about 70%, preferably about 80%, more preferably about 90%, even more preferably about 95%, and most preferably about 97% homology, which encode an active polypeptide. For purposes of the present invention, the degree of homology between two nucleic acid sequences is determined by the Wilbur-Lipman method (Wilbur and Lipman, 1983, *Proceedings of the National Academy of Science USA* 80: 726–730) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=3, gap penalty=3, and windows=20.

Modification of a nucleic acid sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variant sequence may be constructed on the basis of the nucleic acid sequence presented as the polypeptide encoding part of SEQ ID NO:1, e.g., a subsequence thereof, and/or by introduction of nucleotide substitutions which do not give rise to another amino acid sequence of the polypeptide encoded by the nucleic acid sequence, but which correspond to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95–107.

It will be apparent to those skilled in the art that such substitutions can be made outside the regions critical to the function of the molecule and still result in an active polypeptide. Amino acid residues essential to the activity of the polypeptide encoded by the isolated nucleic acid sequence of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081–1085). In the latter technique, mutations are introduced at every positively charged residue in the molecule, and the resultant mutant molecules are tested for pectin acetylesterase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306–312; Smith et al., 1992, *Journal of Molecular Biology* 224: 899–904; Wlodaver et al., 1992, *FEBS Letters* 309: 59–64).

The present invention also relates to isolated nucleic acid sequences encoding a polypeptide of the present invention, which hybridize under very low stringency conditions, preferably low stringency conditions, more preferably medium stringency conditions, more preferably medium-high stringency conditions, even more preferably high stringency conditions, and most preferably very high stringency conditions with a nucleic acid probe which hybridizes under the same conditions with the nucleic acid sequence of SEQ ID NO:1 or its complementary strand; or allelic variants and subsequences thereof (Sambrook et al., 1989, supra), as defined herein.

The present invention also relates to isolated nucleic acid sequences produced by (a) hybridizing a DNA under very low, low, medium, medium-high, high, or very high stringency conditions with (i) nucleotides 76 to 1146 of SEQ ID NO: 1, (ii) a subsequence of (i), or (iii) a complementary strand of (i) or (ii); and (b) isolating the nucleic acid sequence. The subsequence is preferably a sequence of at least 100 nucleotides, and more preferably 200 nucleotides, such as a sequence which encodes a polypeptide fragment which has pectin acetylesterase activity.

Methods for Producing Mutant Nucleic Acid Sequences

The present invention further relates to methods for producing a mutant nucleic acid sequence, comprising introducing at least one mutation into the mature polypeptide coding sequence of SEQ ID NO:1 or a subsequence thereof, wherein the mutant nucleic acid sequence encodes a polypeptide which consists of amino acids 26 to 382 of SEQ ID NO:2 or a fragment thereof which has pectin acetylesterase activity.

The introduction of a mutation into the nucleic acid sequence to exchange one nucleotide for another nucleotide may be accomplished by site-directed mutagenesis using any of the methods known in the art. Particularly useful is the procedure which utilizes a supercoiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with DpnI which is specific for methylated and hemimethylated DNA to digest the parental DNA template and to select for mutation-containing synthesized DNA. Other procedures known in the art may also be used.

Nucleic Acid Constructs

The present invention also relates to nucleic acid constructs comprising a nucleic acid sequence of the present invention operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

"Nucleic acid construct" is defined herein as a nucleic acid molecule, either single- or double-stranded, which is isolated from a naturally occurring gene or which has been modified to contain segments of nucleic acid combined and juxtaposed in a manner that would not otherwise exist in nature. The term nucleic acid construct is synonymous with the term expression cassette when the nucleic acid construct contains all the control sequences required for expression of a coding sequence of the present invention. The term "coding sequence" is defined herein as a nucleic acid sequence which directly specifies the amino acid sequence of its protein product. The boundaries of a genomic coding sequence are generally determined by a ribosome binding site (prokaryotes) located just upstream of the open reading frame at the 5' end of the mRNA and a transcription terminator sequence located just downstream of the open reading frame at the 3' end of the mRNA. A coding sequence can include, but is not limited to, DNA, cDNA, and recombinant nucleic acid sequences.

An isolated nucleic acid sequence encoding a polypeptide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The term "control sequences" is defined herein to include all components which are necessary or advantageous for the expression of a polypeptide of the present invention. Each control sequence may be native or foreign to the nucleic acid sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide. The term "operably linked" is defined herein as a configuration in which a control sequence is appropriately placed at a position relative to the coding sequence of the DNA sequence such that the control sequence directs the expression of a polypeptide.

The control sequence may be an appropriate promoter sequence, a nucleic acid sequence which is recognized by a host cell for expression of the nucleic acid sequence. The promoter sequence contains transcriptional control sequences which mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727–3731), as well as the tac promoter (DeBoer et al., 1983, *Proceedings of the National Academy of Sciences USA* 80: 21–25). Further promoters are described in "Useful proteins from recombinant bacteria" in *Scientific American*, 1980,242: 74–94; and in Sambrook et al., 1989, supra.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

The control sequence may also be a suitable leader sequence, a nontranslated region of an mRNA which is important for translation by the host cell. The leader sequence is operably linked to the 5' terminus of the nucleic acid sequence encoding the polypeptide. Any leader sequence which is functional in the host cell of choice may be used in the present invention.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for Bacillus NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109–137.

In a preferred embodiment, the signal peptide coding region is nucleotides 1 to 75 of SEQ ID NO:1 which encode amino acids 1 to 25 of SEQ ID NO:2.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE) and *Bacillus subtilis* neutral protease (nprT).

Where both signal peptide and propeptide regions are present at the amino terminus of a polypeptide, the propeptide region is positioned next to the amino terminus of a polypeptide and the signal peptide region is positioned next to the amino terminus of the propeptide region.

The nucleic acid constructs of the present invention may also comprise one or more nucleic acid sequences which encode one or more factors that are advantageous for directing the expression of the polypeptide, e.g., a transcriptional activator (e.g., a trans-acting factor), a chaperone, and a processing protease. Any factor that is functional in the host cell of choice may be used in the present invention. The nucleic acids encoding one or more of these factors are not necessarily in tandem with the nucleic acid sequence encoding the polypeptide.

A transcriptional activator is a protein which activates transcription of a nucleic acid sequence encoding a polypeptide (Kudla et al., 1990, *EMBO Journal* 9: 1355–1364; Jarai and Buxton, 1994, *Current Genetics* 26: 2238–244; Verdier, 1990, *Yeast* 6: 271–297). The nucleic acid sequence encoding an activator may be obtained from the gene encoding *Bacillus stearothermophilus* NprA (nprA).

A chaperone is a protein which assists another polypeptide to fold properly (Hartl et al., 1994, *TIBS* 19: 20–25; Bergeron et al., 1994, *TIBS* 19: 124–128; Demolder et al., 1994, *Journal of Biotechnology* 32: 179–189; Craig 1993, *Science* 260: 1902–1903; Gething and Sambrook, 1992, *Nature* 355: 33–45; Puig and Gilbert, 1994, *Journal of Biological Chemistry* 269: 7764–7771; Wang and Tsou, 1993, *The FASEB Journal* 7: 1515–11157; Robinson et al, 1994, *Bio/Technology* 1: 381–384; Jacobs et al., 1993, *Molecular Microbiology* 8: 957–966). The nucleic acid sequence encoding a chaperone may be obtained from the genes encoding *Bacillus subtilis* GroE proteins and *Bacillus subtilis* PrsA. For further examples, see Gething and Sambrook, 1992, supra, and Hartl et al., 1994, supra.

A processing protease is a protease that cleaves a propeptide to generate a mature biochemically active polypeptide (Enderlin and Ogrydziak, 1994, *Yeast* 10: 67–79, Fuller et al., 1989, *Proceedings of the National Academy of Sciences USA* 86: 1434–1438; Julius et al., 1984, *Cell* 37: 1075–1089; Julius et al., 1983, *Cell* 32: 839–852; U.S. Pat. No. 5,702,934). The nucleic acid sequence encoding a processing protease may be obtained from the genes encoding *Saccharomyces cerevisiae* dipeptidylaminopeptidase, *Saccharomyces cerevisiae* Kex2, *Yarrowia lipolytica* dibasic processing endoprotease (xpr6), and *Fusarium oxysporum* metalloprotease (p45 gene).

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance.

The vectors of the present invention preferably contain an element(s) that permits integration of the vector into the host cell's genome or autonomous replication of the vector in the cell independent of the genome.

For integration into the host cell genome, the vector may rely on the nucleic acid sequence encoding the polypeptide or any other element of the vector for integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location (s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli,* and pUB110, pE194, pTA1060, and pAMβ1 permitting replication in Bacillus. The origin of replication may be one having a mutation which makes its functioning temperature-sensitive in the host cell (see, e.g., Ehrlich, 1978, *Proceedings of the National Academy of Sciences USA* 75: 1433).

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid sequence of the invention, which are advantageously used in the recombinant production of the polypeptides. A vector comprising a nucleic acid sequence of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular cells are bacterial cells such as gram positive bacteria including, but not limited to, a Bacillus cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis,* and *Bacillus thuringiensis;* or a Streptomyces cell, e.g., *Streptomyces lividans* and *Streptomyces murinus,* or gram negative bacteria such as *E. coli* and Pseudomonas sp. In a preferred embodiment, the bacterial host cell is a *Bacillus lentus, Bacillus licheniformis, Bacillus stearothermophilus,* or *Bacillus subtilis* cell. In another preferred embodiment, the Bacillus cell is an alkalophilic Bacillus.

The introduction of a vector into a bacterial host cell may, for instance, be effected by protoplast transformation (see, e.g., Chang and Cohen, 1979, *Molecular General Genetics* 168: 111–115), using competent cells (see, e.g., Young and Spizizin, 1961, *Journal of Bacteriology* 81: 823–829, or Dubnau and Davidoff-Abelson, 1971, *Journal of Molecular Biology* 56: 209–221), electroporation (see, e.g., Shigekawa and Dower, 1988, *Biotechniques* 6: 742–751), or conjugation (see, e.g., Koehler and Thorne, 1987, *Journal of Bacteriology* 169: 5771–5278).

Methods of Production

The present invention also relates to methods for producing a polypeptide of the present invention comprising (a) cultivating a strain, which in its wild-type form is capable of producing the polypeptide, to produce a supernatant comprising the polypeptide; and (b) recovering the polypeptide. Preferably, the strain is of the genus Bacillus, and more preferably *Bacillus subtilis*.

The present invention also relates to methods for producing a polypeptide of the present invention comprising (a) cultivating a host cell under conditions conducive for production of the polypeptide; and (b) recovering the polypeptide.

The present invention also relates to methods for producing a polypeptide of the present invention comprising (a) cultivating a host cell under conditions conducive for production of the polypeptide, wherein the host cell comprises a mutant nucleic acid sequence having at least one mutation in the mature polypeptide coding region of SEQ ID NO:1, wherein the mutant nucleic acid sequence encodes a polypeptide which consists of amino acids 26 to 382 of SEQ ID NO:2, and (b) recovering the polypeptide.

In the production methods of the present invention, the cells are cultivated in a nutrient medium suitable for production of the polypeptide using methods known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, thr enzyme assay described herein may be used to determine the activity of the polypeptide.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J. -C. Janson and Lars Ryden, editors, VCH Publishers, New York, 1989).

Plants

The present invention also relates to a transgenic plant, plant part, or plant cell which has been transformed with a nucleic acid sequence encoding a polypeptide having pectin acetylesterase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as festuca, lolium, temperate grass, such as Agrostis, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arahidopsis thaliana*.

Examples of plant parts are stem, callus, leaves, root, fruits, seeds, and tubers. Also specific plant tissues, such as chloroplast, apoplast, mitoehondria, vacuole, peroxisomes, and cytoplasm are considered to be a plant part. Furthermore, any plant cell, whatever the tissue origin, is considered to be a plant part.

Also included within the scope of the present invention are the progeny of such plants, plant parts and plant cells.

The transgenic plant or plant cell expressing a polypeptide of the present invention may be constructed in accordance with methods known in the art. Briefly, the plant or plant cell is constructed by incorporating one or more expression constructs encoding a polypeptide of the present invention into the plant host genome and propagating the resulting modified plant or plant cell into a transgenic plant or plant cell.

Conveniently, the expression construct is a nucleic acid construct which comprises a nucleic acid sequence encoding a polypeptide of the present invention operably linked with appropriate regulatory sequences required for expression of the nucleic acid sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV promoter may be used (Franck et al, 1980, *Cell* 21: 285–294). Organ-specific promoters may be, for example, a promoter from storage sink tissues such as seeds, potato tubers, and fruits (Edwards & Coruzzi, 1990, *Ann. Rev. Genet.* 24: 275–303), or from metabolic sink tissues such as meristems (Ito et al., 1994, *Plant Mol. Biol.* 24: 863–878), a seed specific promoter such as the glutelin, prolamin, globulin, or albumin promoter from rice (Wu et al., 1998, *Plant and Cell Physiology* 39: 885–889), a Vicia faba promoter from the legumin B4 and the unknown seed protein gene from Vicia faba (Conrad et al., 1998, *Journal of Plant Physiology* 152: 708–711), a promoter from a seed oil body protein (Chen et al., 1998, *Plant and Cell Physiology* 39: 935–941), the storage protein napA promoter from *Brassica napus,* or any other seed specific promoter known in the art, e.g., as described in WO 91/14772. Furthermore, the promoter may be a leaf specific promoter such as the rbcs promoter from rice or tomato (Kyozuka et al, 1993, *Plant Physiology* 102: 991–1000, the chlorella virus adenine methyltransferase gene promoter (Mitra and Higgins, 1994, *Plant Molecular Biology* 26: 85–93), or the aldP gene promoter from rice (Kagaya et al., 1995, *Molecular and General Genetics* 248: 668–674), or a wound inducible promoter such as the potato pin2 promoter (Xu et al., 1993, *Plant Molecular Biology* 22: 573–588).

A promoter enhancer element may also be used to achieve higher expression of the enzyme in the plant. For instance, the promoter enhancer element may be an intron which is placed between the promoter and the nucleotide sequence encoding a polypeptide of the present invention. For instance, Xu et al, 1993, supra disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including Agrobacterium-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15–38). However it can also be used for transforming monocots, although other transformation methods are generally preferred for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275–281; Shimamoto, 1994, *Current Opinion Biotechnology* 5: 158–162; Vasil et al, 1992, *Bio/Technology* 10: 667–674). An alternative method for transformation of monocots is based on protoplast transformation as described by Omirulleh et al., 1993, *Plant Molecular Biology* 21: 415–428.

Following transformation, the transformants having incorporated therein the expression construct are selected and regenerated into whole plants according to methods well-known in the art.

The present invention also relates to methods for producing a polypeptide of the present invention comprising (a) cultivating a transgenic plant or a plant cell comprising a nucleic acid sequence encoding a polypeptide having pectin acetylesterase activity of the present invention under conditions conducive for production of the polypeptide; and (b) recovering the polypeptide.

Removal or Reduction of Pectin Acetylesterase Activity

The present invention also relates to methods for producing a mutant cell of a parent cell, which comprises disrupting or deleting a nucleic acid sequence encoding the polypeptide or a control sequence thereof, which results in the mutant cell producing less of the polypeptide than the parent cell when cultivated under the same conditions.

The construction of strains which have reduced pectin acetylesterase activity may be conveniently accomplished by modification or inactivation of a nucleic acid sequence necessary for expression of the polypeptide having pectin acetylesterase activity in the cell. The nucleic acid sequence to be modified or inactivated may be, for example, a nucleic acid sequence encoding the polypeptide or a part thereof essential for exhibiting pectin acetylesterase activity, or the nucleic acid sequence may have a regulatory function required for the expression of the polypeptide from the coding sequence of the nucleic acid sequence. An example of such a regulatory or control sequence may be a promoter sequence or a functional part thereof, i.e., a part which is sufficient for affecting expression of the polypeptide. Other control sequences for possible modification are described above.

Modification or inactivation of the nucleic acid sequence may be performed by subjecting the cell to mutagenesis and selecting or screening for cells in which the pectin acetylesterase producing capability has been reduced. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the cell to be mutagenized in the presence of the mutagenizing agent of choice under suitable conditions, and selecting for cells exhibiting reduced pectin acetylesterase activity or production.

Modification or inactivation of production of a polypeptide of the present invention may be accomplished by introduction, substitution, or removal of one or more nucleotides in the nucleic acid sequence encoding the polypeptide or a regulatory element required for the transcription or translation thereof. For example, nucleotides may be inserted or removed so as to result in the introduction of a stop codon, the removal of the start codon, or a change of the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the nucleic acid sequence to be modified, it is preferred that the modification be performed in vitro as exemplified below.

An example of a convenient way to eliminate or reduce production by a host cell of choice is by gene replacement or gene interruption. In the gene interruption method, a nucleic acid sequence corresponding to the endogenous gene or gene fragment of interest is mutagenized in vitro to produce a defective nucleic acid sequence which is then transformed into the host cell to produce a defective gene. By homologous recombination, the defective nucleic acid sequence replaces the endogenous gene or gene fragment. It may be desirable that the defective gene or gene fragment also encodes a marker which may be used for selection of transformants in which the gene encoding the polypeptide has been modified or destroyed.

Alternatively, modification or inactivation of the nucleic acid sequence may be performed by established anti-sense techniques using a nucleotide sequence complementary to the polypeptide encoding sequence. More specifically, production of the polypeptide by a cell may be reduced or eliminated by introducing a nucleotide sequence complementary to the nucleic acid sequence encoding the polypeptide which may be transcribed in the cell and is capable of hybridizing to the polypeptide mRNA produced in the cell. Under conditions allowing the complementary anti-sense nucleotide sequence to hybridize to the polypeptide mRNA, the amount of polypeptide translated is thus reduced or eliminated.

It is preferred that the cell to be modified in accordance with the methods of the present invention is of microbial origin, for example, a fungal strain which is suitable for the production of desired protein products, either homologous or heterologous to the cell.

The present invention further relates to a mutant cell of a parent cell which comprises a disruption or deletion of a nucleic acid sequence encoding the polypeptide or a control sequence thereof, which results in the mutant cell producing less of the polypeptide than the parent cell.

The polypeptide-deficient mutant cells so created are particularly useful as host cells for the expression of homologous and/or heterologous polypeptides. Therefore, the present invention further relates to methods for producing a homologous or heterologous polypeptide comprising (a) cultivating the mutant cell under conditions conducive for production of the polypeptide; and (b) recovering the polypeptide. The term "heterologous polypeptides" is defined herein as polypeptides which are not native to the host cell, a native protein in which modifications have been made to alter the native sequence, or a native protein whose expression is quantitatively altered as a result of a manipulation of the host cell by recombinant DNA techniques.

In a further aspect, the present invention relates to a method for producing a protein product essentially free of pectin acetylesterase activity by fermentation of a cell which produces both a polypeptide of the present invention as well as the protein product of interest by adding an effective amount of an agent capable of inhibiting pectin acetylesterase activity to the fermentation broth before, during, or after the fermentation has been completed, recovering the product of interest from the fermentation broth, and optionally subjecting the recovered product to further purification.

In a further aspect, the present invention relates to a method for producing a protein product essentially free of pectin acetylesterase activity by cultivating the cell under conditions permitting the expression of the product, subjecting the resultant culture broth to a combined pH and temperature treatment so as to reduce the pectin acetylesterase activity substantially, and recovering the product from the culture broth. Alternatively, the combined pH and temperature treatment may be performed on an enzyme preparation recovered from the culture broth. The combined pH and temperature treatment may optionally be used in combination with a treatment with a pectin acetylesterase inhibitor.

In accordance with this aspect of the invention, it is possible to remove at least 60%, preferably at least 75%, more preferably at least 85%, still more preferably at least 95%, and most preferably at least 99% of the pectin acetylesterase activity. Complete removal of pectin acetylesterase activity may be obtained by use of this method.

The combined pH and temperature treatment is preferably carried out at a pH in the range of 6.5–7 and a temperature in the range of 55–75° C. for a sufficient period of time to attain the desired effect, where typically, 30 to 60 minutes is sufficient.

The methods used for cultivation and purification of the product of interest may be performed by methods known in the art.

The methods of the present invention for producing an essentially pectin acetylesterase-free product is of particular interest in the production of enzymes. The enzyme may be selected from, e.g., an amylolytic enzyme, lipolytic enzyme, proteolytic enzyme, cellulytic enzyme, oxidoreductase, or plant cell-wall degrading enzyme. Examples of such enzymes include an aminopeptidase, amylase, amyloglucosidase, carbohydrase, carboxypeptidase, catalase, cellulase, chitinase, cutinase, cyclodextrin glycosyltransferase, deoxyribonuclease, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectolytic enzyme, peroxidase, phytase, phenoloxidase, polyphenoloxidase, proteolytic enzyme, ribonuclease, transferase, transglutaminase, or xylanase. The pectin acetylesterase-deficient cells may also be used to express heterologous proteins of pharmaceutical interest such as hormones, growth factors, receptors, and the like.

It will be understood that the term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from pectin acetylesterase activity which is produced by a method of the present invention.

Compositions

In a still further aspect, the present invention relates to compositions comprising a polypeptide of the present invention and a suitable carrier. Preferably, the compositions are enriched in a polypeptide of the present invention. In the present context, the term "enriched" indicates that the pectin acetylesterase activity of the composition has been increased, e.g., with an enrichment factor of 1.1. Suitable carriers are well known in the art.

The composition may comprise a polypeptide of the invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, another pectolytic enzyme(s), peptidoglutaminase, peroxidase, phytase, polyphenoloxidase, proteolytic enzyme, ribonuclease, transglutaminase, or xylanase. The additional enzyme(s) may be producible by means of any microorganism.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Uses

The present invention also relates to methods for degrading a pectic substance, comprising contacting the pectic substance with an effective amount of one or more polypeptides of the present invention under conditions suitable for degrading the substance. The one or more polypeptides may be contained in a composition comprising the polypeptide(s) and a suitable carrier, as described above. The composition may further comprise other enzymes useful in the degradation of pectic substances, such as other pectolytic enzymes, cellulases, and hemicellulases. The other pectolytic enzymes may include endo- and exo-pectin lyase(s), endo- and exo-polymethylgalacturonase(s), endo- and exo-pectate lyase(s), endo- and exo-polygalacturonase(s), pectin methyl esterase (s), rhamnogalacturonan acetylesterase(s) and/or rhamnogalacturonase, or any other enzyme known to degrade pectic substances.

The polypeptides of the present invention and compositions thereof may be used for the degradation of soluble and insoluble pectins with varying degrees of esterification for viscosity reduction, clarification, depectinization, and maceration of plant tissue using methods well known in the art.

In a preferred embodiment, the polypeptides are used as an agent, alone or in combination with other enzymes, for the degradation or modification of acetylated pectins.

In another preferred embodiment, the polypeptides are used, alone or in combination with other enzymes, as an agent for degradation or modification of plant cell walls.

In another preferred embodiment, the polypeptides are used together with other enzymes specific to acylated or partially acylated pectin. These further enzymes include all enzymes, which attack acetylated and partially acetylated pectin with a higher specificity than they attack deacetylated pectins, including enzymes that attack the pectin backbone by endo and/or exo attack, or enzymes which attach the side branches. Such an enzyme may be rhamnogalacturonan acetylesterase. See, for example, WO 93/20190.

In another preferred embodiment, the polypeptides are used together with other enzymes specific to deacylated or partially deacylated pectin. These further enzymes include all enzymes, which attack deacetylated and partially deacylated pectin with a higher specificity than they attack acetylated pectins, including enzymes that attack the pectin backbone by endo and/or exo attack, or enzymes which attach the side branches.

In another preferred embodiment, the polypeptides are used together with other enzymes specific to acylated or partially acylated pectin and other enzymes specific to deacylated or partially deacylated pectin.

The dosage of the polypeptide(s) and conditions necessary for degrading pectin-containing substances may be determined using methods well known in the art. A polypeptide of the present invention is typically added in an amount corresponding to 0.01–100 mg enzyme protein per kg of pectin-containing material.

Signal Peptide

The present invention also relates to nucleic acid constructs comprising a gene encoding a protein operably linked to a nucleic acid sequence consisting of nucleotides 1 to 75 of SEQ ID NO:1 encoding a signal peptide consisting of amino acids 1 to 25 of SEQ ID NO:2, wherein the gene is foreign to the nucleic acid sequence.

The present invention also relates to recombinant expression vectors and recombinant host cells comprising such a nucleic acid construct.

The present invention also relates to methods for producing a protein comprising (a) cultivating such a recombinant host cell under conditions suitable for production of the protein; and (b) recovering the protein.

The nucleic acid sequence may be operably linked to foreign genes with other control sequences. Such other control sequences are described above.

The protein may be native or heterologous to a host cell. The term "protein" is not meant herein to refer to a specific length of the encoded product and, therefore, encompasses peptides, oligopeptides, and proteins. The term "protein" also encompasses two or more polypeptides combined to form the encoded product. The proteins also include hybrid polypeptides which comprise a combination of partial or complete polypeptide sequences obtained from at least two different proteins wherein one or more may be heterologous or native to the host cell. Proteins further include naturally occurring allelic and engineered variations of the above mentioned proteins and hybrid proteins.

Preferably, the protein is a hormone, hormone variant, enzyme, receptor or a portion thereof, antibody or a portion thereof, or reporter. In a more preferred embodiment, the protein is an oxidoreductase, transferase, hydrolase, lyase, isomerase, or ligase. In an even more preferred embodiment, the protein is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, lipase, mannosidase, mutanase, oxidase, pectolytic enzyme, peroxidase, phytase, polyphenoloxidase, proteolytic enzyme, ribonuclease, transglutaminase, or xylanase.

The gene may be obtained from any prokaryotic, eukaryotic, or other source. For purposes of the present invention, the term "obtained from" as used herein in connection with a given source shall mean that the protein is produced by the source or by a cell in which a gene from the source has been inserted.

The present invention is further described by the following examples which should not be construed as limiting the scope of the invention.

EXAMPLES

Chemicals used as buffers and substrates were commercial products of at least reagent grade.

Bacterial strains

*E. coli* DH5α, *E. coli* JM101, *Bacillus subtilis* A164 (ATCC 6051A), *Bacillus subtilis* 168 (Bacillus Stock Center, Columbus, Ohio), and *Bacillus subtilis* PL1801 spoIIE::Tn917 (amyE, apr, npr).

Primers and Oligos

All primers and oligos were synthesized on an Applied Biosystems Model 394 Synthesizer (Applied Biosystems, Inc., Foster City, Calif.) according to the manufacturer's instructions.

Example 1
Isolation and characterization of pectin acetylesterase gene from *Bacillus subtilis* 168

Genomic DNA was isolated from *Bacillus subtilis* 168 using the QIAGEN bacterial genomic DNA isolation protocol (QIAGEN, Valencia, Calif.) according to the manufacturer's instructions.

Oligonucleotide primers 1 and 2 shown below were used to amplify the pectin acetylesterase coding region from *Bacillus subtilis* 168 genomic DNA by PCR. Primer 1 incorporated a SacI site and the ribosome binding site of a Bacillus serine protease (SAVINASE™, Novo Nordisk A/S, Bagsvaerd, Denmark, hereinafter referred to as the SAVINASE™ gene) upstream of the pectin acetylesterase coding region, and primer 2 incorporated a NotI site downstream of the pectin acetylesterase coding region.

The amplification reaction (50 µl) contained approximately 200 ng of *Bacillus subtilis* 168 genomic DNA, 0.5 µM of each primer, 200 µM each of dATP, dCTP, dGTP, and dTTP, 1×PCR buffer, 3 mM $MgCl_2$, and 0.625 units of AmpliTaq Gold DNA polymerase (PE Applied Biosystems, Foster City, Calif.). The reaction was cycled in a RoboCycler 40 Temperature Cycler (Stratagene Cloning Systems, La Jolla, Calif.) programmed for one cycle at 95° C. for 9 minutes; 30 cycles each at 95° C. for 1 minute, 55° C. for 1 minute, and 72° C. for 1 minute; and a final cycle at 72° C. for 3 minutes.

Primer 1:
5'-CGAGCTCTATAAAAATGAGGAGGGAACCGAAT GAAAAAATGGATGGCAGCG-3' (SEQ ID NO. 3)

Primer 2:
5'-GCGGCCGCTTAAAAGCCAGCGATTCCCTG-3' (SEQ ID NO. 4)

The PCR product was cloned using the TOPO™ TA Cloning Kit (Invitrogen, Carlsbad, Calif.) according to the manufacturer's instructions. Plasmid DNA was isolated from *E. coli* TOP10 transformants using the QIAprep 8 Plasmid Kit (QIAGEN, Valencia, Calif.) according to manufacturer's instructions. A plasmid containing the desired insert was identified by restriction analysis using enzymes EcoRI, BglI, DraI, PvuI, NotI, and SacI and was designated pCR2.1-yxiM. The *E. coli* TOP10 colony containing the pCR2.1-yxiM plasmid was isolated, and plasmid DNA was prepared for sequencing using a QIAGEN Plasmid Kit according to the manufacturer's instructions. *E. coli* SURE cells (Stratagene Cloning Systems, La Jolla, Calif.) were transformed with this plasmid, and one transformant was designated MDT28 and deposited with the NRRL Culture Collection.

DNA sequencing was performed with an Applied Biosystems Model 377 XL Automated DNA Sequencer using dye-terminator chemistry and synthetic oligonucleotides based on the published yxiM gene sequence (Shevchik et al., 1997, supra).

DNA sequence analysis confirmed the sequence of pectin acetylesterase gene with two discrepancies relative to the published sequence of the yxiM gene (Shevchik et al., 1997, supra): The G residue reported at position 247 of the yxiM coding sequence was a C residue, and the C residue reported at position 447 of the yxiM coding sequence was a G residue. DNA sequence analysis of five independent PCR products generated using primers 1 and 2 with *Bacillus subtilis* 168 genomic DNA using the same methods described above confirmed the C residue at position 247, indicating that the published G residue is an error. This sequence change results in an amino acid change of the published glutamate residue at position 83 to a glutamine residue. The nucleotide change at position 447 does not affect the amino acid sequence of the encoded protein.

The pectin acetylesterase clone had an open reading frame of 1146 bp encoding a polypeptide of 382 amino acids. The nucleotide sequence (SEQ ID NO:1) and deduced amino acid sequence (SEQ ID NO:2) are shown in FIG. 1. Using the SignalP program (Nielsen et al., 1997, *Protein Engineering* 10: 1–6), a signal peptide of 25 residues was predicted corresponding to nucleotides 1 to 75 of SEQ ID NO:1.

A comparative alignment of pectin acetylesterase amino acid sequences was undertaken using the Clustal method (Higgins, 1989, *CABIOS* 5: 151–153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5.

The comparative alignment showed that the *Bacillus subtilis* pectin acetylesterase shared regions of identity of 14.9% with the pectin acetylesterase from *Erwinia chrysanthemi* (EMBL Y09828) and 14.4% with the rhamnogalacturonan acetylesterase from *Aspergillus aculeatus* (EMBL X89714).

Example 2
Construction of pDG268MCS pDG268 (Antoniewski, et al., 1990, *Journal of Bacteriology* 172: 86–93) was digested with Tth111I and EcoRI. The largest plasmid fragment of approximately 6020 bp was gel-purified using the QIAquick™ DNA purification kit (QIAGEN, Valencia, Calif.) according to the manufacturer's instructions. The recovered DNA was then ligated with the following synthetic polylinker shown below to introduce unique SfiI and BamHI sites into the plasmid.

```
      SfiI  ApaI SmaI AatII HindIII ClaI BamHI  NotI           (SEQ ID NOS. 5 and 6, respectively)
5'-AATTGGCCTTAAGGGCCCGGGACGTCAAGCTTATCGATGCGGATCCGCGGCCGC-3'

3'-CCGGAATTCCCGGGCCCTGCAGTTCGAATAGCTACGCCTAGGCGCCGGCGC-5'
```

*E. coli* DH5α was transformed with the ligation mixture and ampicillin resistant transformants were selected on 2×YT plates (composed per liter of 16 g Tryptone, 10 g yeast extract, 5 g NaCl, and 15 g agar) supplemented with 100 µg of ampicillin per ml. Plasmid DNA was purified according to Sambrook et al., 1989, supra, and digested with SfiI and NotI to identify plasmids which contained these sites and, by implication, the polylinker shown above (pDG268 does not contain these two restriction sites). Several plasmids were identified which contained both restriction sites and in addition were approximately 3.0 kb smaller than pDG268 as a result of replacing the lacZ gene of pDG268 with the synthetic polylinker. One such plasmid was chosen and designated pDG268MCS (FIG. 2).

Example 3
Construction of pHP13ampMCS pHP13-amp, a variant of pHP13 (Haima et al., 1987, *Molecular and General Genetics* 209: 335–342), was constructed by digesting pUC9 with AatII, blunting with Klenow fragment and dNTPs, and then digesting with HindIII. The larger 2.2 kb fragment was gel-purified with a Qiaex kit (QIAGEN, Valencia, Calif.). pHP13 was digested with HpaI (which cuts within the erythromycin resistance gene), blunted, and then digested with HindIII. The larger 3.0 kb fragment released from pHP13 was then ligated to the 2.1 kb pUC9 fragment containing the pUC9 origin of replication and ampicillin resistance gene. The ligation mixture was transformed into E. coli DH5α, and ampicillin resistant transformants were selected on 2×YT plates supplemented with 100 µg of ampicillin per ml. Plasmid DNA was purified from several transformants as described in Example 1. A plasmid designated pHP13amp was recovered from one of the transformants.

Plasmid pHP13amp was digested with EcoRI and HindIII and the pUC9 MCS was replaced with a new MCS created by annealing 100 pmol of the following polylinker in 50 mM NaCl, 10 mM Tris pH 7.5, and 1 mM EDTA, boiling for 5 minutes, and cooling slowly to room temperature over a 2 hour time period:

```
         SfiI  ApaI SmaI AatII SacI HindIII NotI NcoI SalI        (SEQ ID NOS. 7 and 8, respectively)
5'-AGCTAGGCCTTAAGGGCCCGGGACGTCGAGCTCAAGCTTGCGGCCGCCATGGTCGACG-3'

3'-TCCGGAATTCCCGGGCCCTGCAGCTCGAGTTCGAACGCCGGCGGTACCAGCTGCTTAA-5'
```

Figure 3:
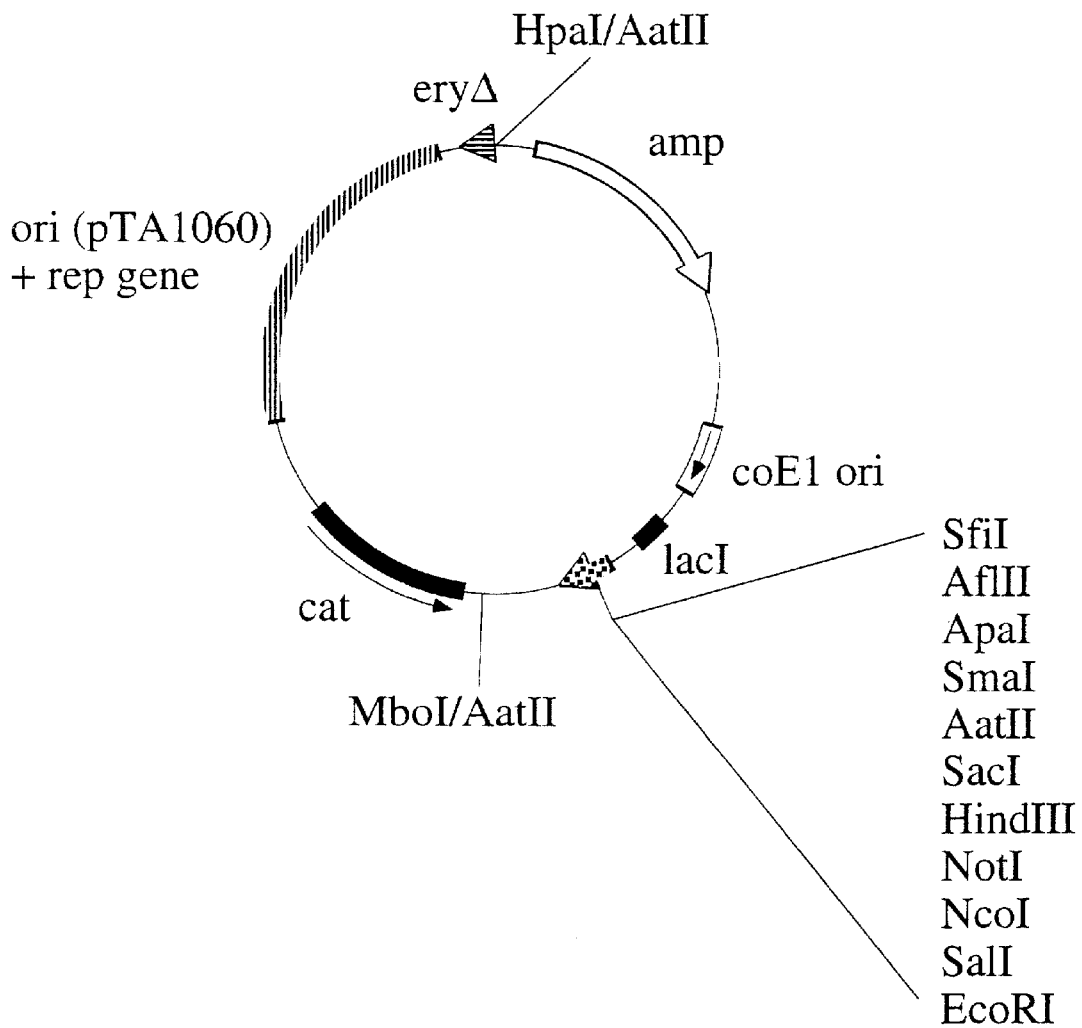
FIG. 3 shows a restriction map of pHP13amp-MCS.

E. coli DH5α was transformed with the ligation mix and ampicillin resistant transformants were selected on 2×YT plates supplemented with 100 µg of ampicillin per ml. Plasmid DNA was purified from several transformants and digested with NotI and SacI. Plasmids which were cleaved with these enzymes contained the synthetic polylinker. One such plasmid was identified and designated pHP13amp-MCS (FIG. 3). This plasmid was further verified by DNA sequencing through the polylinker region.

Example 4
Isolation of the SAVINASE™ serine protease gene

The gene encoding a Bacillus serine protease known as SAVINASE™ (Novo Nordisk A/S, Bagsvaerd, Denmark) was PCR-amplified using plasmid pSX222 (U.S. Pat. No. 5,621,089) as template DNA and the following two primers (restriction sites are underlined):

```
         ApaI      SacI
5'-CCTCGGGCCCATCTGAGCTCTATAAAAATGAGGAGGG-3'         (SEQ ID NO. 9)

BamHI
5'-CCTCGGATCCATACACAAAAAAACGCT-3'                   (SEQ ID NO. 10)
```

The amplification reaction (100 µl) consisted of the following components: 50 ng of pSX222, 50 pmol of each primer, 1×Taq DNA polymerase buffer (Boehringer Mannheim, Indianapolis, Ind.), 200 µM each of dATP, dTTP, dGTP, and dCTP, and 2.5 units of Taq DNA polymerase (Perkin-Elmer Corp., Branchburg, N.J.). The amplification conditions were one cycle at 95° C. for 3 minutes, 30 cycles each at 95° C. for 1 minute, 55° C. for 1 minute, and 72° C. for 1.5 minutes, and a final cycle at 72° C. for 5 minutes.

Figure 4:
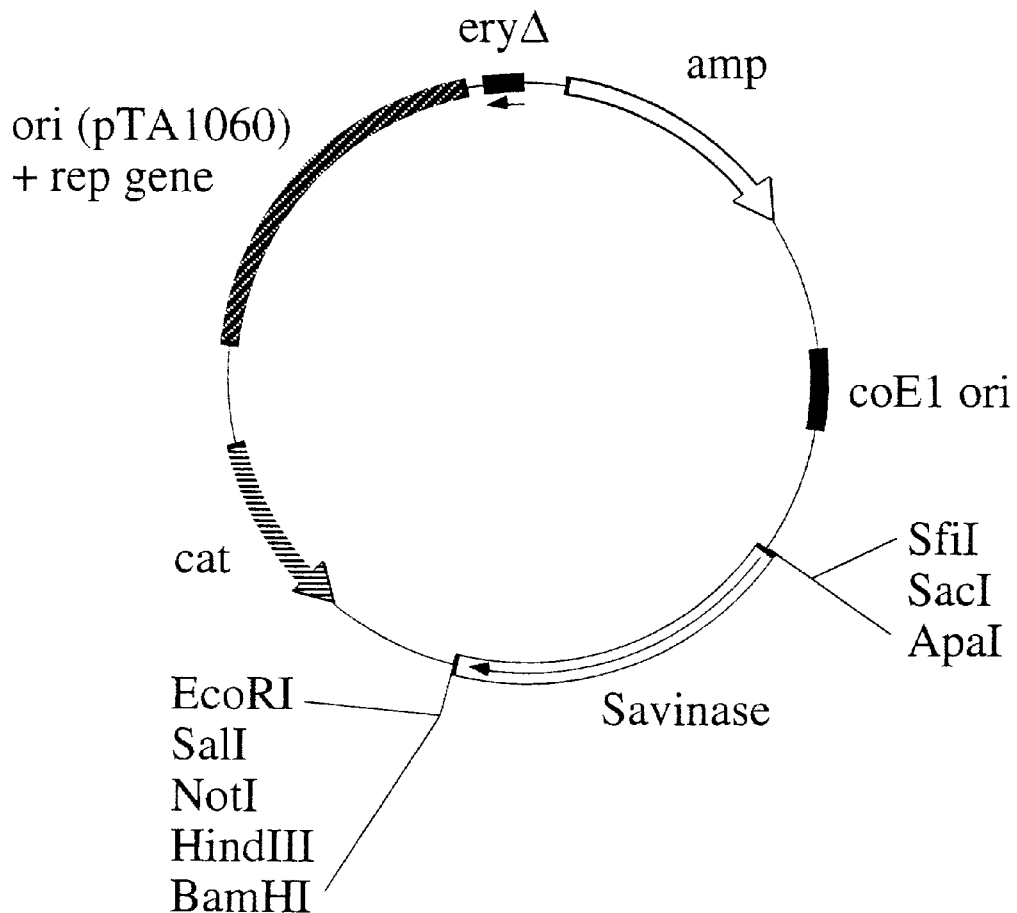
FIG. 4 shows a restriction map of pHP13amp-SAV.

The approximately 1230 bp PCR product was subcloned directly into the pCRII vector (Invitrogen, Carlsbad, Calif.) according to the manufacturer's instructions. The sequence of the gene was verified by DNA sequencing using gene-specific primers. Once verified, the plasmid was digested with BamHI, filled in with Klenow fragment, and digested with ApaI, and the fragment harboring the SAVINASE™ gene was then ligated into the ApaI/Ecl136II site of pHP13ampMCS. E. coli DH5(was transformed with this ligation mixture, and ampicillin resistant transformants were selected on 2×YT plates supplemented with 100 µg of ampicillin per ml. A plasmid designated pHP13amp-SAV (FIG. 4) was isolated from one of the transformants and verified by DNA sequencing using construct-specific primers. The BamHI site was regenerated as a result of this ligation.

Example 5
Construction of pUC18-Pr$_{cryIIIA}$/cryIIIAstab/cryIIIA

The promoter of the cryIIIA gene which encodes a Bacillus thuringiensis subsp. tenebrionis crystal protein CryIIIA was PCR amplified from chromosomal DNA isolated according to Pitcher et al., 1989, Letters in Applied Microbiology 8: 151–156 from the Bacillus thuringiensis subsp. tenebrionis strain NB125 described in WO 95/02695 using the following primers:

```
         SmaI
5'-GAGACCCGGGAGCTTTCAGTGAAGTACGTG-3'(SEQ ID NO. 11)

5'-GGGGCGTTACAATTCAAAG-3'            (SEQ ID NO. 12)
```

The amplification reaction (100 µl) consisted of the following components: 50 ng of Bacillus thuringiensis subsp. tenebrionis NB125 chromosomal DNA, 50 pmol of each primer, 1×Pfu polymerase buffer (Stratagene Cloning Systems, La Jolla, Calif.), 200 µM each of dATP, dTTP, dGTP, and dCTP, and 1.0 unit of Pfu polymerase (Stratagene Cloning Systems, La Jolla, Calif.). The amplification conditions were one cycle at 95° C. for 3 minutes; 30 cycles each at 95° C. for 1 minute, 50° C. for 1 minute, and 72° C. for 1.5 minutes; and a final cycle at 72° C. for 5 minutes. The approximately 1000 bp PCR product was digested with SmaI and HindIII and ligated into the SmaI/HindIII site of pUC18. E. coli DH5α was transformed with this ligation mixture, and ampicillin resistant transformants were selected on 2×YT plates supplemented with 100 µg of ampicillin per ml. A plasmid designated pUC18-Pr$_{cryIIIA}$ was isolated from one of the ampicillin resistant transformants.

Figure 5:
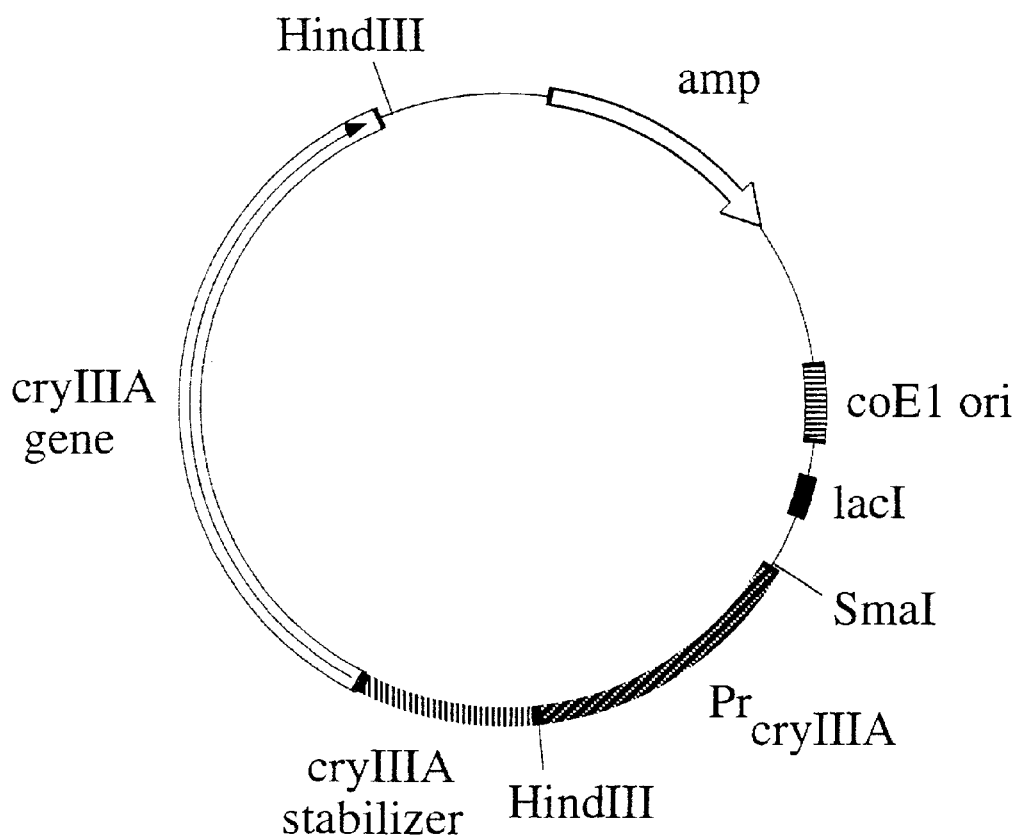
FIG. 5 shows a restriction map of pUC18-Pr$_{cryIIIA}$/cryIIIAstab/cryIIIA.

Plasmid pUC118-cryIIIA (WO 95/02695) was digested with HindIII and the approximately 3000 bp HindIII fragment harboring the cryIIIA gene and mRNA stabilizing sequence was gel-purified using the QIAquick™ DNA purification kit according to the manufacturer's instructions. This fragment was ligated into the HindIII site of pUC$^{18}$-Pr$_{cryIIIA}$. E. coli DH5α was transformed with this ligation mixture, and ampicillin resistant transformants were selected on 2×YT plates supplemented with 100 µg of ampicillin per ml. A plasmid designated pUC18-Pr$_{cryIIIA}$/cryIIIAstab/cryIIIA (FIG. 5) was isolated from one of the ampicillin resistant transformants. The correct orientation of the fragment was confirmed by digesting the plasmid with EcoRI.

Example 6

Construction of a cryIIIA promoter-cryIIIA mRNA stabilizer-SAVINASE™ gene expression cassette The promoter and mRNA stabilizing sequence of the cryIIIA gene were PCR amplified using plasmid pUC18-Pr$_{cryIIIA}$/cryIIIAstab/cryIIIA as DNA template and the two primers described below:

```
      ApaI
5'-GGGCCCTCGAAACGTAAGATGAAACCT-3'  (SEQ ID NO. 13)

SacI
5'-GAGCTCCATAATACATAATTTTCAAACTG-3'(SEQ ID NO. 14)
```

The amplification reaction (100 μl) consisted of the following components: 50 ng of pUC18-PrcryIIIA/cryIIIAstab, 50 pmol of each primer, 1×Taq polymerase buffer, 200 μM each of dATP, dTTP, dGTP, and dCTP, and 1.0 unit of Taq polymerase. The amplification conditions were one cycle at 95° C. for 3 minutes; 30 cycles each at 95° C. for I minute, 55° C. for 1 minute, and 72° C. for 1.5 minutes; and a final cycle at 72° C. for 5 minutes.

The approximately 630 bp PCR product was cloned into the pCRII vector according to the manufacturer's instructions to generate pCRII-Pr$_{cryIIIA}$/cryIIIAstab, which was verified by DNA sequencing, using M13 sequencing primers and cryIIIA-specific primers.

The approximately 630 bp SfiI-SacI fragment of pCRII-Pr$_{cryIIIA}$/cryIIIAstab bearing the cryIIIA promoter with the mRNA stabilizer sequence was gel purified and ligated to SfiI/SacI-digested pHP13amp-SAV. *E. coli* DH5α was transformed with this ligation mixture, and ampicillin resistant transformants were selected on 2×YT plates supplemented with 100 μg of ampicillin per ml. A plasmid designated pHP13amp-Pr$_{cryIIIA}$/cryIIIAstab/SAV was purified from one of the ampicillin resistant transformants.

Figure 6:
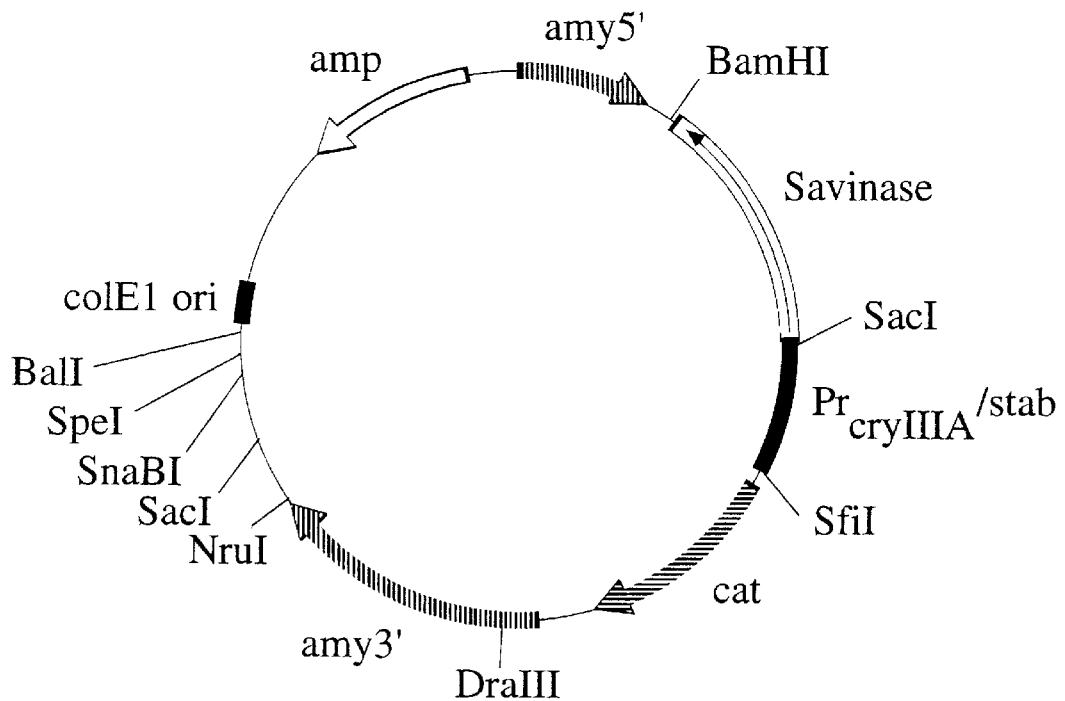
FIG. 6 shows a restriction map of pDG268MCS-Pr$_{cryIIIA}$/cryIIIAstab/SAV.

The approximately 1850 bp SfiI-BamHI fragment of pHP 13amp-Pr$_{cryIIIA}$/cryIIIAstab/SAV bearing the Pr$_{cryIIIA}$/cryIIIAstab/SAV cassette was gel purified using the QIAquick™ DNA purification kit according to the manufacturer's instructions and ligated to SfiI/BamHI-digested pDG268MCS. *E. coli* DH5α was transformed with this ligation mixture, and ampicillin resistant transformants were selected on 2×YT plates supplemented with 100 μg of ampicillin per ml. A plasmid designated pDG268MCS-Pr$_{cryIIIA}$/cryIIIAstab/SAV (FIG. 6) was purified from one of the ampicillin resistant transformants.

Example 7

Construction of pDG268MCSΔ-Pr$_{cryIIIA}$/cryIIIAstab/SAV pDG268MCS-Pr$_{cryIIIA}$/cryIIIAstab/SAV was digested with SnaBI and NruI (both restriction sites flank the SacI site of the vector), ligated, and transformed into *E. coli* DH5α. Ampicillin resistant transformants were selected on 2×YT plates supplemented with 100 μg of ampicillin per ml.

Figure 7:
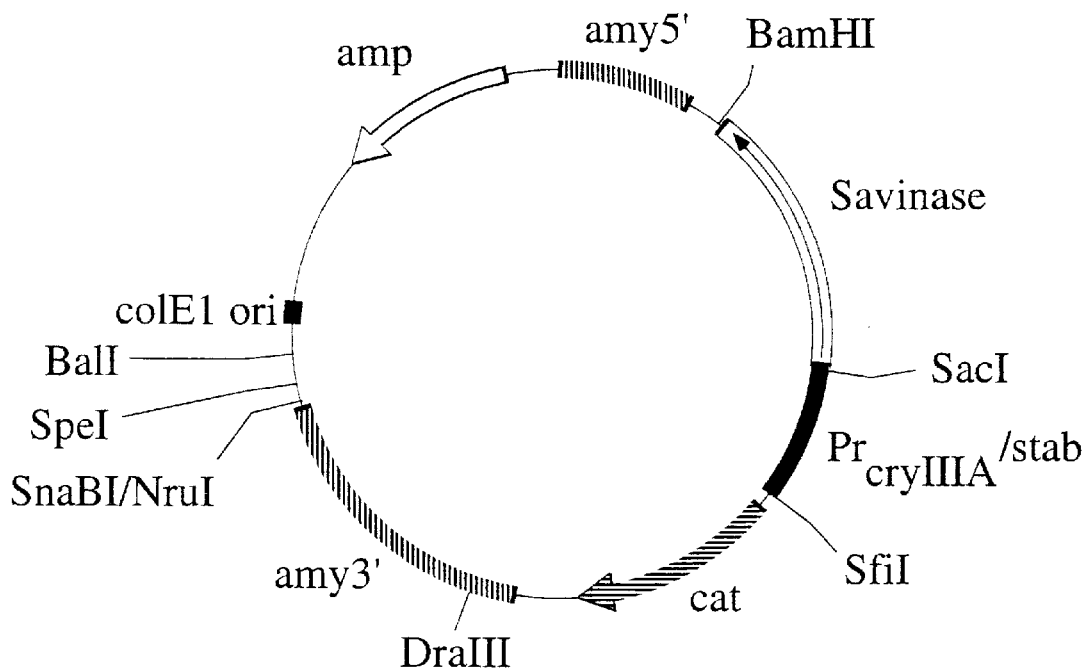
FIG. 7 shows a restriction map of pDG268MCSΔ-Pr$_{cryIIIA}$/cryIIIAstab/SAV.

Plasmid DNA was purified from several transformants. The plasmid DNA was digested with SacI to identify plasmids which were deleted for the SacI site located in the vector sequence and thus cleaved only once due to the SacI site downstream of the cryIIIA promoter. Such a plasmid was identified and designated pDG268MCSΔ-Pr$_{cryIIIA}$/cryIIIAstab/SAV (FIG. 7).

Example 8

Figure 8:
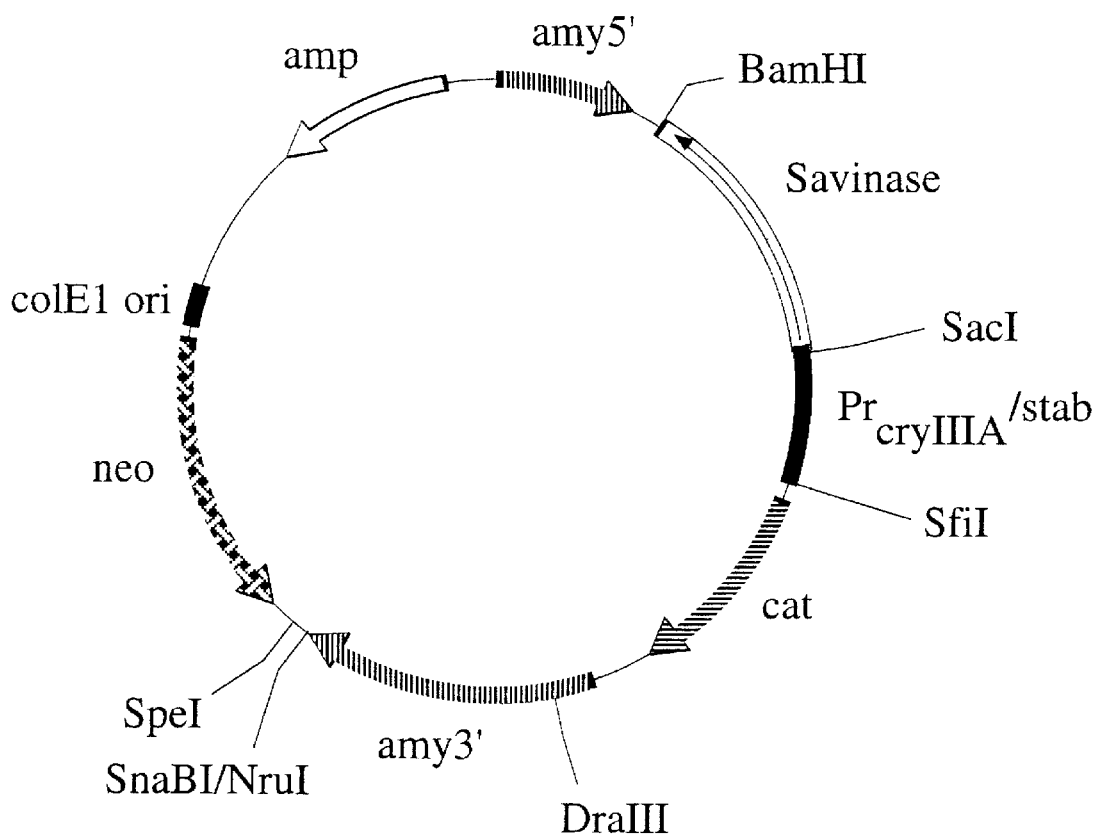
FIG. 8 shows a restriction map of pDG268MCSΔneo-Pr$_{cryIIIA}$/cryIIIAstab/SAV.

Construction of pDG268MCSΔ-Pr$_{cryIIIA}$/cryIIIAstab/SAV pDG268MCSΔ-Pr$_{cryIIIA}$/cryIIIAstab/SAV was digested with BalI and treated with calf intestinal alkaline phosphatase. Plasmid pBEST501 (Itaya et al., 1989, *Nucleic Acids Research* 17: 4410) was digested with PstI and NotI, treated with T4 DNA polymerase I to generate blunt ends, and agarose gel purified to isolate a fragment harboring the neomycin resistance marker. The gel-purified fragment and BalI-digested plasmid were ligated together and transformed into *E. coli* DH5α. Ampicillin resistant transformants were selected on 2×YT plates supplemented with 100 μg of ampicillin per ml. The selected transformants were patched onto LB plates supplemented with 50 μg of neomycin per ml to identify neomycin resistant transformants. Plasmid DNA was purified from a few of the neomycin resistant transformants and digested with BglII (cuts twice due to the additional BglII site introduced with the neomycin resistance marker) yielding two fragments in the 4 kb range and with BamHI (which is predicted to cut once downstream of the SAVINASE™ protease gene) yielding a fragment of approximately 8 kb. Such a plasmid was identified and designated pDG268MCSΔneo-Pr$_{cryIIIA}$/cryIIIAstab/SAV (FIG. 8).

Example 9

Construction of a "consensus" amyQ promoter

The following two oligonucleotides were annealed together and extended with Klenow fragment to generate a 68 bp double stranded fragment containing mutations (*) in the –10 and –35 regions of the amyQ promoter (highlighted in bold letters):

```
                    SOE        **                      *
5'-GGAATAAAGGGGGGTTGACATTATTTTACTGATATGTATAATAT-3'         (SEQ ID NO. 15)

SacI
3'-AATAAAATGACTATACATATTATATTAAACATATTCTTTTACCTCGAG-5'    (SEQ ID NO. 16)
```

A second double-stranded fragment comprising 137 bp of the upstream region of the amyQ promoter was generated by PCR using the following to primers:

```
      SfiI
5'-GGCCTTAAGGGCCTGCA-3'          (SEQ ID NO. 17)

SOE
5'-TGTCAACCCCCCTTTATTCCTT-3'     (SEQ ID NO. 18)
```

Both double-stranded DNA fragments were then fused together by traditional SOE (splicing by overlap extension) PCR methods to generate a mutated version of the amyQ promoter designated "consensus" amyQ. SOE overlaps are underlined and labeled. The primers used in the SOE reaction to obtain the full-length fragment were as follows:

```
        SfiI
5'-GGCCTTAAGGGCCTGCA-3'                    (SEQ ID NO. 17)

SacI
5'-GAGCTCCATTTTCTTATACAAATTATAT-3' (SEQ ID NO. 19).
```

The SOE reaction (50 µl) consisted of the following components: 50 ng of the 68 bp SOE fragment and 50 ng of the 137 bp SOE fragment, 1×Taq polymerase buffer, 200 µM each of dATP, dTTP, dGTP, and dCTP, and 2.5 units of Taq DNA polymerase. The conditions were one cycle at 95° C. for 3 minutes; 30 cycles each at 95° C. for 1 minute, 55° C. for 1 minute, and 72° C. for 1.5 minutes; after the third cycle 50 pmole of each of the two primers described above were added during the remaining 27 cycles to amplify the 185 bp promoter fragment. A final cycle was performed at 72° C. for 5 minutes.

The approximately 185 bp PCR product was subcloned directly into the pCRII vector according to the manufacturer's instructions and verified by DNA sequencing yielding pCRII-Pr$_{\text{"consensus" amyQ}}$, using forward and reverse M13 sequencing primers.

The sequence of the entire amyQ promoter including flanking restriction sites is shown in FIG. 9 (SEQ ID NO. 20). The following mutations were introduced into the nucleic acid sequence containing the wild-type amyQ promoter (SEQ ID NO. 20) to generate the "consensus" amyQ promoter (SEQ ID NO. 21): T to A and T to C in the –35 region (with respect to the transcription start site) at positions 135 and 136, respectively, and an A to T change in the –10 region at position 156 of SEQ ID NO. 20. Also a T to A change was inadvertently made at position 116 approximately 20 base pairs upstream of the –35 region as shown in FIG. 9 (SEQ ID NO. 22). This change apparently had no detrimental effect on promoter function since it is well removed from the critical –10 and –35 regions.

Example 10

Construction of a short "consensus" amyQ promoter-SAVINASE™ gene expression cassette The short "consensus" amyQ promoter was PCR amplified from pCRII-Pr$_{\text{"consensis" amyQ}}$ using the following oligonucleotide primers:

5'-GGCCTTAAGGGCCTGCTGTCCAGACTGTCCGCT-3' (SEQ ID NO. 23)
5'-GAGCTCCATTTTCTTATACAAATTATAT-3' (SEQ ID NO. 19)

The amplification reaction (100 µl) consisted of the following components: 50 ng of pCRII-Pr$_{\text{"consensus" amyQ}}$, 50 pmole of each primer, 1×Taq polymerase buffer, 200 µM each of dATP, dTTP, dGTP, and dCTP, and 1.0 unit of Taq polymerase. The amplification conditions were one cycle at 95° C. for 3 minutes; 30 cycles each at 95° C. for 1 minute, 50° C. for 1 minute, and 72° C. for 1.5 minutes; and a final cycle at 72° C. for 5 minutes.

Figure 10:
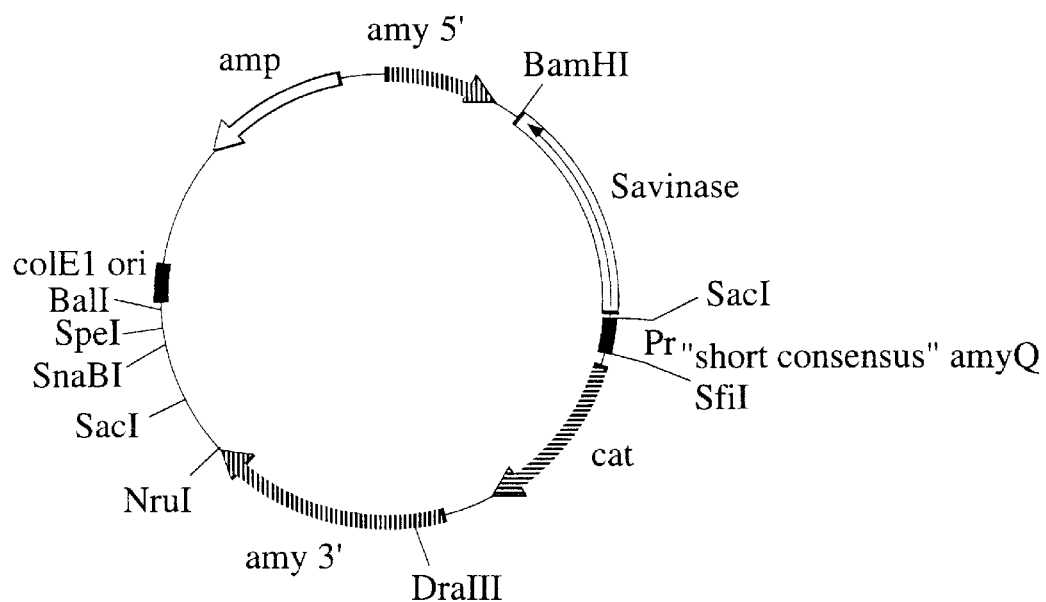
FIG. 10 shows a restriction map of pDG268MCS-Pr$_{short}$ "consensus" amyQ/SAV.

The approximately 100 bp PCR product was cloned into the pCRII vector according to the manufacturer's instructions, yielding plasmid pCRII-Pr$_{\text{short "consensus" amyQ}}$, which was verified by DNA sequencing, using forward and reverse M13 sequencing primers.

pCRII-Pr$_{\text{short "consensus" amyQ}}$ was digested with SfiI and SacI, and the approximately 100 bp fragment bearing the promoter was isolated by gel electrophoresis. pHP13amp-SAV was digested with SfiI and SacI, and the approximately 6430 bp vector fragment was isolated by gel electrophoresis. The purified fragments were ligated together, Bacillus subtilis PL1801 spoIIE::Tn917 was transformed with this ligation mixture, and chloramphenicol resistant transformants were selected on Tryptose Blood Agar Base (TBAB) plates supplemented with 5 µg of chloramphenicol per ml. A plasmid designated pHP13amp-Pr$_{\text{short "consensus" amyQ}}$/SAV was purified from a chloramphenicol resistant transformant that produced a zone of clearing on a TBAB plate supplemented with 1% non-fat dry milk. The plasmid was verified by digestion with SfiI and BamHI.

pHP13amp-Pr$_{\text{short "consensus" amyQ}}$/SAV was digested with SfiI and BamHI, and the approximately 1330 bp fragment bearing the Pr$_{\text{short "consensus" amyQ}}$/SAV cassette was isolated by gel electrophoresis. pDG268MCS was digested with SfiI and BamHI, and the approximately 6040 bp vector fragment was isolated by gel electrophoresis, The purified fragments were ligated together, E. coli DH5α was transformed with the ligation, and ampicillin resistant transformants were selected on LB plates supplemented with 100 µg of ampicillin per ml. A plasmid designated pDG268MCS-Pr$_{\text{short "consensus" amyQ}}$/SAV (FIG. 10) was purified from one of the ampicillin-resistant transformants and verified by digestion with SfiI and BamHI followed by gel electrophoresis.

Example 11

Figure 11:
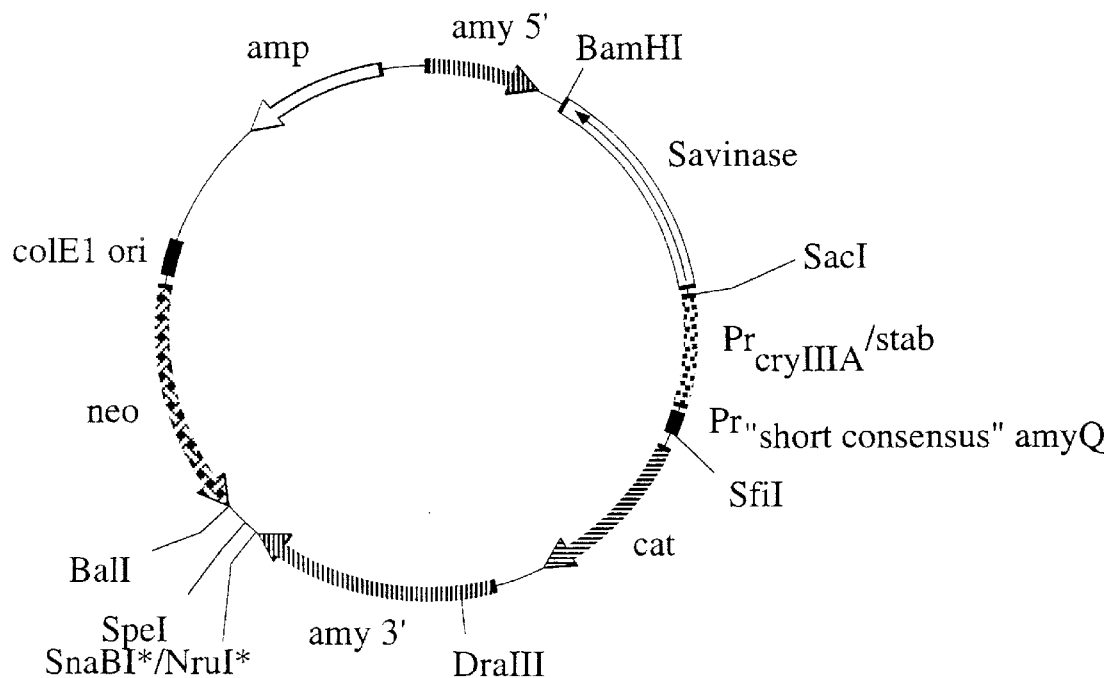
FIG. 11 shows a restriction map of pDG268MCSΔneo-Pr$_{short}$ "consensus" amyQ/Pr$_{cryIIIA}$/cryIIIAstab/SAV.
Figure 12:
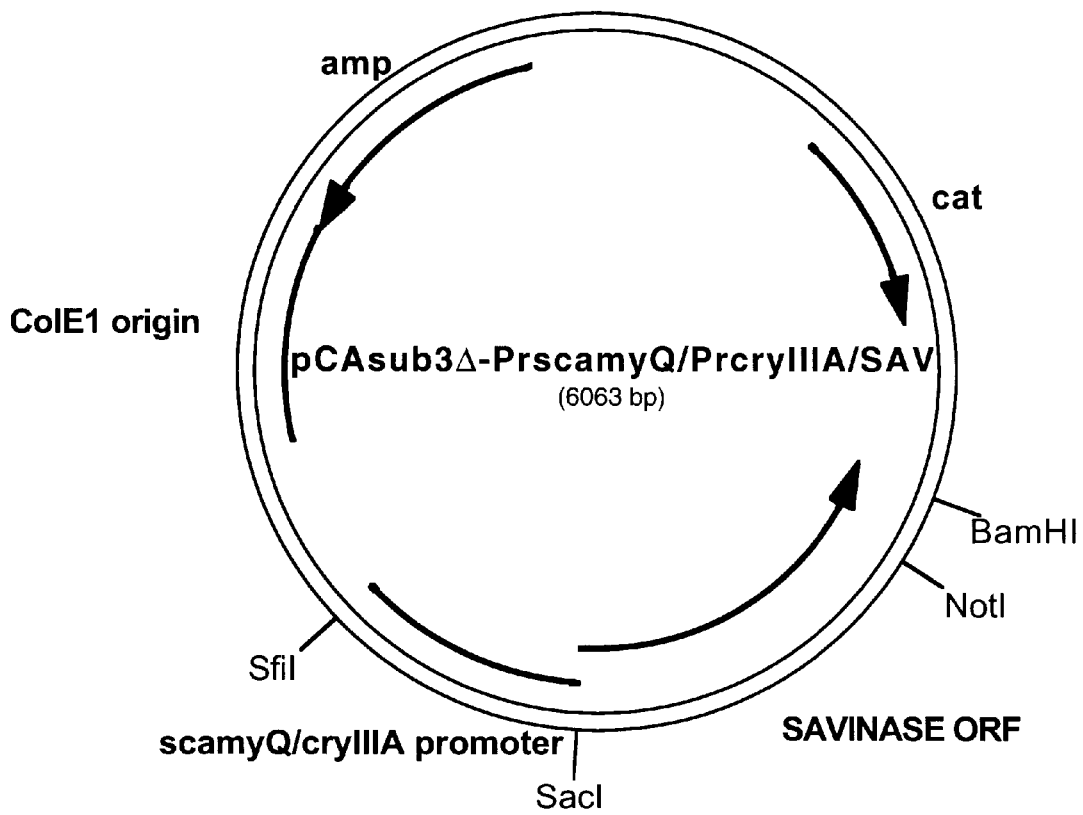
FIG. 12 shows a restriction map of pCAsub3Δ-Pr"$_{short}$ consensus amyQ/Pr$_{cryIIIA}$/SAV.

Construction of a tandem short "consensus" amyQ-cryIIIA promoter-cryIIIA mRNA stabilizer-SAVINASE™ gene expression cassette pDG268MCSΔneo-Pr$_{cryIIIA}$/cryIIIAstab/SAV was digested with SfiI and BamHI, and the approximately 6780 bp vector fragment was isolated by gel electrophoresis. pDG268MCS-Pr$_{\text{short "consensus" amyQ}}$/SAV was digested with SfiI and BamHI, and the approximately 1300 bp expression cassette fragment was isolated by gel electrophoresis. The purified fragments were ligated together and transformed into E. coli DH5α cells. Ampicillin resistant transformants were selected on 2×YT plates supplemented with 100 µg of ampicilllin per ml. A plasmid designated pDG268MCSΔneo-Pr$_{\text{short "consensus" amyQ}}$/SAV (FIG. 10) was purified from one of the ampicillin resistant transformants and verified by digestion with NcoI followed by gel electrophoresis.

pDG268MCSΔneo-Pr$_{cryIIIA}$/cryIIIAstab/SAV was digested with SfiI, treated with Klenow fragment to generate blunt ends, and digested with DraIII. The approximately 7060 bp vector fragment was isolated by gel electrophoresis. pDG268MCSΔneo-Pr$_{\text{short "consensus" amyQ}}$/SAV was digested with Ecl136II and DraIII, and the approximately 1540 bp fragment bearing the short "consensus" amyQ promoter was isolated by gel. The purified fragments were ligated together and transformed into E. coli DH5α cells. Ampicillin resistant transformants were selected on 2×YT plates supplemented with 100 µg of ampicillin per ml. A plasmid designated pDG268MCSΔneo-Pr$_{\text{short "consensus" amyQ}}$/Pr$_{cryIIIA}$/cryIIIAstab/SAV (FIG. 11) was purified from one of the ampicillin resistant transformants and verified by digestion with NcoI followed by gel electrophoresis.

Example 12

Construction of pCAsub3Δ-Pr$_{\text{short consensus amyQ}}$/cryIIIA/SAV

Plasmid p2419MCS5-cat (WO 98/22598) was digested with SacI and SalI and treated with Klenow fragment of E. coli DNA polymerase I and dNTPs to generate blunt ends. The approximately 4240 bp vector fragment was gel-purified using the QIAquick Gel Purification Kit (QIAGEN, Valencia, Calif.) and treated with T4 DNA ligase. E. coli DH5α was transformed with this ligation mixture, and ampicillin resistant transformants were selected on 2×YT plates supplemented with 100 µg of ampicillin per ml. A plasmid designated p2419catΔ was purified from one of the ampicillin resistant transformants and verified by DNA sequencing using the same method described in Example 1.

Genomic DNA was isolated from *Bacillus subtilis* A164 using the QIAGEN bacterial genomic DNA isolation protocol. Oligonucleotide primers 3 and 4 shown below were used to amplify a fragment of the amyE gene from *Bacillus subtilis* A164 genomic DNA by PCR. Primer 3 incorporated a NotI site, and primer 4 incorporated an Asp718 site.

Primer 3: 5'-GCGGCCGCGATTTCCAATGAG-3' (SEQ ID NO. 24)

Primer 4: 5'-GGTACCTGCATTTGCCAGCAC-3' (SEQ ID NO. 25)

The PCR was performed as described in Example 1. The PCR product was cloned using the TOPO TA Cloning Kit according to the manufacturer's instructions. Plasmid DNA was isolated from *E. coli* TOP10 transformants using the QIAprep 8 Plasmid Kit according to manufacturer's instructions. A plasmid containing the desired insert was identified by restriction analysis using enzyme EcoRI and designated pCR2.1-amyE.

p2419catΔ was digested with NotI and Asp718, and the approximately 4240 bp vector fragment was gel-purified using the QIAquick Gel Purification Kit. pCR2.1-amyE was digested with NotI and Asp718, and the approximately 805 bp amyE fragment was gel-purified using the QIAquick Gel Purification Kit. The gel-purified fragments were ligated using the Rapid DNA Ligation Kit (Roche Molecular Biochemicals, Indianapolis, Ind.). *E. coli* DH5α was transformed with this ligation, and ampicillin resistant transformants were selected on 2×YT plates supplemented with 100 μg of ampicillin per ml. Plasmid DNA was isolated from *E. coli* DH5α transformants using the QIAprep 8 Plasmid Kit according to manufacturer's instructions. A plasmid containing the desired insert was identified by restriction analysis using enzyme NotI and designated pCAsub3.

pCAsub3 was digested with BamHI and SphI to remove the amyE fragment and treated with T4 DNA polymerase and dNTPs to generate blunt ends. The approximately 4140 bp vector fragment was gel-purified using the QIAquick Gel Purification Kit and treated with T4 DNA ligase (restoring the BamHI site). *E. coli* DH5α was transformed with this ligation mixture, and ampicillin resistant transformants were selected on 2×YT plates supplemented with 100 μg of ampicillin per ml. Plasmid DNA was isolated from *E. coli* transformants using the QIAprep 8 Plasmid Kit according to manufacturer's instructions. A plasmid lacking the amyE fragment was identified and designated pCAsub3Δ.

pCAsub3Δ was digested with SfiI and BamHI, and the approximately 4110 bp vector fragment was gel-purified using the QIAquick Gel Purification Kit. pDG268MCSΔneo-Pr$_{short\ "consensus"\ amyQ}$/Pr$_{cryIIIA}$/cryIIIAstab/SAV was digested with SfiI and BamHI, and the approximately 1950 bp fragment bearing $Pr_{short\ “consensus”\ amyQ}$/$Pr_{cryIIIA}$/cryIIIAstab/SAVwas gel-purified using the QIAquick Gel Purification Kit. The gel-purified fragments were ligated using the Rapid DNA Ligation Kit. *E. coli* DH5α was transformed with this ligation, and ampicillin resistant transformants were selected on 2×YT plates supplemented with 100 μg of ampicillin per ml. Plasmid DNA was isolated from *E. coli* transformants using the QIAprep 8 Plasmid Kit according to manufacturer's instructions. A plasmid containing the desired insert was identified by restriction analysis using enzyme EcoRI and designated pCAsub3Δ-$Pr_{short\ “consensus”\ amyQ}$/$Pr_{cryIIIA}$/cryIIIAstab/SAV (FIG. 12).

Example 13

Construction of a $Pr_{“short\ consensus\ amyQ}$/$Pr_{cryIIIA}$/cryIIIAstab/yxiM integrant pCAsub3A-$Pr_{short\ “consensus”\ amyQ}$/$Pr_{cryIIIA}$/cryIIIAstab/SAV was digested with SacI and NotI to remove most of the SAVINASE™ gene coding region, and the approximately 5030 bp vector fragment was gel-purified using the QIAquick Gel Purification Kit. pCR2.1-yxiM was digested with SacI and NotI, and the approximately 1180 bp pectin acetylesterase gene-bearing fragment was gel-purified using the QIAquick Gel Purification Kit. The gel-purified fragments were ligated using the Rapid DNA Ligation Kit. *Bacillus subtilis* PL 1801 spoIIE::Tn917 was transformed with this ligation, and chloramphenicol-resistant transformants (with the $Pr_{short\ “consensus”\ amyQ}$/$Pr_{cryIIIA}$/cryIIIAstab/yxiM cassette integrated presumably at the pectin acetylesterase gene locus) were selected on TBAB plates supplemented with 5 μg of chloramphenicol per ml. One such integrant was selected, and tandem duplications of the integrated DNA were induced by streaking an integrant on TBAB plates supplemented with progressively higher concentrations of chloramphenicol, to a maximum of 60 μg chloramphenicol per ml. This strain was designated *Bacillus subtilis* MDT25.

Genomic DNA was isolated from *Bacillus subtilis* MDT25 using the same method described in Example 1. *Bacillus subtilis* A164A5 (WO 98/22598) was transformed with *Bacillus subtilis* MDT25 genomic DNA, and chloramphenicol resistant integrants were selected on TBAB plates supplemented with 5 μg chloramphenicol per ml. One such integrant was isolated and designated *Bacillus subtilis* MDT26.

Example 14

Production of pectin acetylesterase

*Bacillus subtilis* strains MDT25 and MDT26 -were grown in 50 ml of Lactobacilli MRS Broth (Difco Laboratories, Detroit, Mich.) in 250 ml shake flasks at 37° C. and 250 rpm for 28 hours. Supernatants were recovered by centrifugation at 7000 rpm for 5 minutes. Supernatant samples were run on Novex SDS-PAGE (Novex, San Diego, Calif.), and protein bands were visualized by staining with Coomassie blue. An intense band corresponding to a protein of the expected size for mature pectin acetylesterase (39 kdal; amino acids 26–382) was seen in both samples.

Approximately 4.2 μl of the crude enzyme (10 μg/ml) was incubated at 30° C. for 15 hours in a thermomixer with 0.5 ml of sugar beet pectin (10 mg/ml) or 50 mM triacetin in Tris-HCl pH 8.0 buffer. Acetic acid release was measured by using the enzyme-linked Boehringer Mannheim Acetic Acid Determination Kit (Boehringer Mannheim GMbH, Mannheim, Germany) according to manufacturer's suggested conditions. The results showed that the enzyme preparation was active toward sugar beet pectin and triacetin.

Example 15

Purification and characterization of recombinant pectin acetylesterase

Bacillus strain MDT25 was cultivated for 48 hours at pH 6.8–7.2, 37° C. in a 3 liter fermentation tank (1300 rpm) using suitable carbon and nitrogen sources and salts. A volume of 1.5 liters of whole culture broth was centrifuged using a GS-3 rotor and Sorvall RC-5B centrifuge (Dupont, Wilmington, Del.) at 6000 rev/min for 30 minutes. The supernatant was recovered and centrifuged for an additional 30 minutes to remove any sedimented material. The supernatant was first filtered through 1.0 μm CF/B Whatman (Whatman, Inc., Fairfield, N.J.) filter paper followed by a Whatman 0.45 μm PVDF Syringe Filter (Whatman, Inc., Fairfield, N.J.) with frequent filter changes. A total volume of 1.0 liter of filtered supernatant was recovered. A 20 ml volume of the supernatant pre-diluted 1:2 with water to a conductivity of 6.0 mS was further diluted with 120 ml water to a conductivity of 1.47 mS. The diluted supernatant was filtered through a Millipore Express 0.22 μm filter (Millipore, Bedford, Mass.).

Q-Sepharose Big Beads (Pharmacia Biotech, Inc., Piscataway, N.J.) were prepared in a XK-26 column with a volume of approximately 60 ml of resin. The column was pre-equilibrated with 500 ml of 20 mM Tris-HCl buffer pH 8.0. The supernatant sample was then loaded onto the column, followed by washing with 20 mM Tris-HCl buffer pH 8.0 until baseline was achieved. A 600 ml gradient was run from 0 to 0.50 M NaCl-20 mM Tris-HCl pH 8.0 at a flow rate of 5 ml/minute for 120 minutes. Fractions of 10 ml and 130 ml of flow-through were collected and assayed using 4.5 mM p-nitrophenyl acetate in 100 mM MOPS-4 mM calcium chloride pH 7.5 at 25° C. and 405 nm. Greater than 85% of the total activity was detected in the flow-through. Active fractions and flow-through were also analyzed by SDS PAGE electrophoreses using a 8–16% Tris-glycine gel (Novex, San Diego, Calif.). The purified protein was found to be in the flow-through at a purity of greater than 98% by SDS-PAGE. SDS-PAGE of the purified pectin acetylesterase revealed a major band at approximately 40 kDa molecular weight based on Novex Mark12™ SDS page markers (Novex, San Diego, Calif.).

The purified pectin acetylesterase was also shown to be active toward triacetin by assaying for activity using 100 mM triacetin (Sigma Chemical Co., St Louis, Mo.) in 20 mM Tris-HCl pH 8.0 for 10 minutes at 30° C. Acetic acid release was measured by using the Boehringer Mannheim Acetic Acid Determination Kit according to manufacturer's suggested conditions and modified for 96-well plates.

Example 16

N-terminal sequencing of the purified pectin acetylesterase

N-terminal sequencing of the purified pectin acetylesterase obtained as described in Example 15 was performed on an Applied Biosystems 476A Protein Sequencer (Perkin Elmer/Applied Biosystems Division, Foster City, Calif.) with on-line HPLC and liquid phase trifluoroacetic acid (TFA) delivery. The pectin acetylesterase preparation was subjected to SDS-PAGE using Novex 8–16% Tris-glycine SDS-PAGE gels according to manufacturer's suggested conditions. The gel was transblotted to PVDF membranes (Novex, San Diego, Calif.) for 2 hours at 25 volts in 10% methanol in 10 mM CAPS p11 11.0 buffer. The PVDF membrane was stained in 0.1% Commassie Blue R250 in 40% methanol/1% acetic acid and the observed band excised. The excised band was sequenced from a blot cartridge using sequencing reagents (Perkin Elmer/Applied Biosystems Division, Foster City, Calif.). Detection of phenylthiohydantoin-amino acids was accomplished by on-line HPLC using Buffer A containing 3.5% tetrahydrofuran in water with 18 ml of the Premix concentrate (Perkin Elmer/Applied Biosystems Division, Foster City, Calif.) containing acetic acid, sodium acetate, and sodium hexanesulfonate and Buffer B containing acetonitrile. Data were collected and analyzed on a Macintosh IIsi computer using Applied Biosystems 610 Data Analysis software. Amino acid identifications were performed by the operator by comparing the chromatograms against a light source.

N-terminal sequencing of the 40 kDa excised band was determined to be as follows:
AEPKVYQFDFGSGSMEPGYIGVRASD (a subsequence of SEQ ID NO. 2)

Deposit of Biological Material

The following biological material has been deposited under the terms of the Budapest Treaty with the Agricultural Research Service Patent Culture Collection, Northern Regional Research Center, 1815 University Street, Peoria, Ill., 61604, and given the following accession number:

| Deposit | Accession Number | Date of Deposit |
|---|---|---|
| E. coli MDT28 (pCR2.1-yxiM) | NRRL B-30151 | June 30, 1999 |

The strain has been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. An isolated polypeptide having pectin acetylesterase activity comprising amino acids 26 to 382 of SEQ ID NO: 2.

2. The polypeptide of claim 1 comprising the amino acid sequence of SEQ ID NO: 2.

3. The polypeptide of claim 1 consisting of the amino acid sequence of SEQ ID NO: 2.

4. The polypeptide of claim 1 consisting of amino acids 26 to 382 of SEQ ID NO: 2.

5. The polypeptide of claim 1, which is encoded by the nucleic acid sequence contained in plasmid pCR2.1-yxiM which is contained in E. coli NRRL B-30151.

6. A method for producing the polypeptide of claim 1 comprising (a) cultivating a strain to produce a supernatant comprising the polypeptide; and (b) recovering the polypeptide.

7. A method for degrading a pectic substance, comprising contacting the pectic substance with an effective amount of a composition comprising a suitable carrier and one or more polypeptides of claim 1 under conditions suitable for degrading the pectic substance.

* * * * *

SEQUENCE LISTING

<160> NUMBER OF SEQ ID NOS: 25

<210> SEQ ID NO 1
<211> LENGTH: 1149
<212> TYPE: DNA
<213> ORGANISM: Bacillus subtilis -continued

```
<400> SEQUENCE: 1
atgaaaaaat ggatggcagc ggttttttgtg atgatgctga tgctgtgttt tggcgggatt      60
gagaatgtga aggcggcgga gccgaaggtg tatcagtttg actttggaag cggttcgatg     120
gagcctggtt atattggtgt cagggcgtct gatcggtatg accggtcaaa gggctacggt     180
tttcaaacac cggagaatat gagggatgtg gcggcatccg gggctggtgt gaagagtgat     240
gcggttcagt ttttagcgta tgggacgaaa agcaataaca cgtttaatgt tgatctcccg     300
aatggccttt atgaggtgaa ggtgacgctt ggcaatacga caagggccag tgtggcagcg     360
gagggcgtgt ttcaggtcat caatatgaca ggggatggcg cggaggatac gttccaaatt     420
cccgtcaccg acgggcagct gaatctcctg gtgacagagg gaaaggcagg caccgctttt     480
acgctcagcg ccttgaaaat aaagaaattg tctgatcagc cggtaacgaa tcgaaccatt     540
tatgtcggcg gcgactcgac ggtgtgcaat tattatccgc tcaacagcag caagcaggcg     600 ggctggggc  agatgctgcc tcactatatc gataaacaca ccttttcaagt gagaaacatg     660 gcgtctggcg gcagatcgc  gagagggttc agaaatgatg acagcttga  ggcgattctg     720 aagtatatta acccggaga  ttattttatg ttgcagcttg cattaatga  cacaaatccg     780 aagcataaag aatctgaagc ggagtttaaa gaggtgatgc gtgatatgat tcgtcaggta     840
aaagcgaaag gagcggacgt catcctatca acgcctcagg gccgggcaac cgatttttact    900 tctgaaggca tccattcgtc tgtaaaacaga tggtacaggg cctctatttt  agctttggcc    960
gaagaggaaa aaacatatct cattgactta aatgtcctca gctcggcata ctttacatcg    1020
atcggtccgg aaagaacact cgggctttat atggatggag atacgctgca cccgaatcgc    1080
gcggggcccg acgcactggc gcgattggct gttcaggagc taaaacgcca gggaatcgct    1140
ggcttttaa                                                           1149
```

<210> SEQ ID NO 2
<211> LENGTH: 382
<212> TYPE: PRT
<213> ORGANISM: Bacillus subtilis

<400> SEQUENCE: 2

```
Met Lys Lys Trp Met Ala Ala Val Phe Val Met Met Leu Met Leu Cys
 1               5                  10                  15

Phe Gly Gly Ile Glu Asn Val Lys Ala Ala Glu Pro Lys Val Tyr Gln
                20                  25                  30

Phe Asp Phe Gly Ser Gly Ser Met Glu Pro Gly Tyr Ile Gly Val Arg
            35                  40                  45

Ala Ser Asp Arg Tyr Asp Arg Ser Lys Gly Tyr Gly Phe Gln Thr Pro
        50                  55                  60

Glu Asn Met Arg Asp Val Ala Ala Ser Gly Ala Gly Val Lys Ser Asp
65                  70                  75                  80

Ala Val Gln Phe Leu Ala Tyr Gly Thr Lys Ser Asn Asn Thr Phe Asn
                85                  90                  95

Val Asp Leu Pro Asn Gly Leu Tyr Glu Val Lys Val Thr Leu Gly Asn
                100                 105                 110

Thr Ala Arg Ala Ser Val Ala Ala Glu Gly Val Phe Gln Val Ile Asn
            115                 120                 125

Met Thr Gly Asp Gly Ala Glu Asp Thr Phe Gln Ile Pro Val Thr Asp
        130                 135                 140

Gly Gln Leu Asn Leu Leu Val Thr Glu Gly Lys Ala Gly Thr Ala Phe
```

-continued

```
                145                 150                 155                 160

Thr Leu Ser Ala Leu Lys Ile Lys Lys Leu Ser Asp Gln Pro Val Thr
                165                 170                 175

Asn Arg Thr Ile Tyr Val Gly Gly Asp Ser Thr Val Cys Asn Tyr Tyr
                180                 185                 190

Pro Leu Asn Ser Ser Lys Gln Ala Gly Trp Gly Gln Met Leu Pro His
                195                 200                 205

Tyr Ile Asp Lys His Thr Phe Gln Val Arg Asn Met Ala Ser Gly Gly
                210                 215                 220

Gln Ile Ala Arg Gly Phe Arg Asn Asp Gly Gln Leu Glu Ala Ile Leu
225                 230                 235                 240

Lys Tyr Ile Lys Pro Gly Asp Tyr Phe Met Leu Gln Leu Gly Ile Asn
                245                 250                 255

Asp Thr Asn Pro Lys His Lys Glu Ser Glu Ala Glu Phe Lys Glu Val
                260                 265                 270

Met Arg Asp Met Ile Arg Gln Val Lys Ala Lys Gly Ala Asp Val Ile
                275                 280                 285

Leu Ser Thr Pro Gln Gly Arg Ala Thr Asp Phe Thr Ser Glu Gly Ile
                290                 295                 300

His Ser Ser Val Asn Arg Trp Tyr Arg Ala Ser Ile Leu Ala Leu Ala
305                 310                 315                 320

Glu Glu Glu Lys Thr Tyr Leu Ile Asp Leu Asn Val Leu Ser Ser Ala
                325                 330                 335

Tyr Phe Thr Ser Ile Gly Pro Glu Arg Thr Leu Gly Leu Tyr Met Asp
                340                 345                 350

Gly Asp Thr Leu His Pro Asn Arg Ala Gly Ala Asp Ala Leu Ala Arg
                355                 360                 365

Leu Ala Val Gln Glu Leu Lys Arg Gln Gly Ile Ala Gly Phe
                370                 375                 380

<210> SEQ ID NO 3
<211> LENGTH: 51
<212> TYPE: DNA
<213> ORGANISM: Bacillus subtilis

<400> SEQUENCE: 3
cgagctctat aaaaatgagg agggaaccga atgaaaaaat ggatggcagc g         51

<210> SEQ ID NO 4
<211> LENGTH: 29
<212> TYPE: DNA
<213> ORGANISM: Bacillus subtilis

<400> SEQUENCE: 4
gcggccgctt aaaagccagc gattccctg                                   29

<210> SEQ ID NO 5
<211> LENGTH: 54
<212> TYPE: DNA
<213> ORGANISM: Bacillus subtilis

<400> SEQUENCE: 5
aattggcctt aagggcccgg gacgtcaagc ttatcgatgc ggatccgcgg ccgc       54

<210> SEQ ID NO 6
<211> LENGTH: 51
<212> TYPE: DNA
<213> ORGANISM: Bacillus subtilis
```

<400> SEQUENCE: 6
ccggaattcc cgggccctgc agttcgaata gctacgccta ggcgccggcg c    51

<210> SEQ ID NO 7
<211> LENGTH: 58
<212> TYPE: DNA
<213> ORGANISM: Bacillus subtilis

<400> SEQUENCE: 7
agctaggcct taagggcccg gacgtcgag ctcaagcttg cggccgccat ggtcgacg    58

<210> SEQ ID NO 8
<211> LENGTH: 58
<212> TYPE: DNA
<213> ORGANISM: Bacillus subtilis

<400> SEQUENCE: 8
tccggaattc ccgggccctg cagctcgagt tcgaacgccg gcggtaccag ctgcttaa    58

<210> SEQ ID NO 9
<211> LENGTH: 37
<212> TYPE: DNA
<213> ORGANISM: Bacillus subtilis

<400> SEQUENCE: 9
ctccgggccc atctgagctc tataaaaatg aggaggg    37

<210> SEQ ID NO 10
<211> LENGTH: 27
<212> TYPE: DNA
<213> ORGANISM: Bacillus subtilis

<400> SEQUENCE: 10
cctcggatcc atacacaaaa aaacgct    27

<210> SEQ ID NO 11
<211> LENGTH: 30
<212> TYPE: DNA
<213> ORGANISM: Bacillus subtilis

<400> SEQUENCE: 11
gagacccggg agctttcagt gaagtacgtg    30

<210> SEQ ID NO 12
<211> LENGTH: 19
<212> TYPE: DNA
<213> ORGANISM: Bacillus subtilis

<400> SEQUENCE: 12
ggggcgttac aattcaaag    19

<210> SEQ ID NO 13
<211> LENGTH: 27
<212> TYPE: DNA
<213> ORGANISM: Bacillus subtilis

<400> SEQUENCE: 13
gggccctcga aacgtaagat gaaacct    27

<210> SEQ ID NO 14
<211> LENGTH: 29
<212> TYPE: DNA

```
<213> ORGANISM: Bacillus subtilis

<400> SEQUENCE: 14
gagctccata atacataatt ttcaaactg                                29

<210> SEQ ID NO 15
<211> LENGTH: 44
<212> TYPE: DNA
<213> ORGANISM: Bacillus subtilis

<400> SEQUENCE: 15
ggaataaagg ggggttgaca ttattttact gatatgtata atat               44

<210> SEQ ID NO 16
<211> LENGTH: 48
<212> TYPE: DNA
<213> ORGANISM: Bacillus subtilis

<400> SEQUENCE: 16
aataaaatga ctatacatat tatattaaac atattctttt acctcgag           48

<210> SEQ ID NO 17
<211> LENGTH: 17
<212> TYPE: DNA
<213> ORGANISM: Bacillus subtilis

<400> SEQUENCE: 17
ggccttaagg gcctgca                                             17

<210> SEQ ID NO 18
<211> LENGTH: 22
<212> TYPE: DNA
<213> ORGANISM: Bacillus subtilis

<400> SEQUENCE: 18
tgtcaacccc cctttattcc tt                                       22

<210> SEQ ID NO 19
<211> LENGTH: 28
<212> TYPE: DNA
<213> ORGANISM: Bacillus subtilis

<400> SEQUENCE: 19
gagctccatt ttcttataca aattatat                                 28

<210> SEQ ID NO 20
<211> LENGTH: 185
<212> TYPE: DNA
<213> ORGANISM: Bacillus subtilis

<400> SEQUENCE: 20
ggccttaagg gcctgcaatc gattgtttga gaaagaaga agaccataaa aatacctgt    60 ctgtcatcag acagggtatt ttttatgctg tccagactgt ccgctgtgta aaaaatagga  120
ataagggggg gttgttatta ttttactgat atgtaaaata taatttgtat aagaaaatgg  180
agctc                                                              185

<210> SEQ ID NO 21
<211> LENGTH: 185
<212> TYPE: DNA
<213> ORGANISM: Bacillus subtilis

<400> SEQUENCE: 21
```

-continued

```
ggccttaagg gcctgcaatc gattgtttga gaaaagaaga agaccataaa aataccttgt        60
ctgtcatcag acagggtatt ttttatgctg tccagactgt ccgctgtgta aaaaaaagga      120
ataaaggggg gttgacatta ttttactgat atgtataata taatttgtat aagaaaatgg      180
agctc                                                                  185
```

<210> SEQ ID NO 22
<211> LENGTH: 185
<212> TYPE: DNA
<213> ORGANISM: Bacillus subtilis

<400> SEQUENCE: 22

```
ggccttaagg gcctgcaatc gattgtttga gaaaagaaga agaccataaa aataccttgt        60
ctgtcatcag acagggtatt ttttatgctg tccagactgt ccgctgtgta aaaatagga       120 ataaaggggg gttgacatta ttttactgat atgtataata taatttgtat aagaaaatgg      180
agctc                                                                  185
```

<210> SEQ ID NO 23
<211> LENGTH: 33
<212> TYPE: DNA
<213> ORGANISM: Bacillus subtilis

<400> SEQUENCE: 23

```
ggccttaagg gcctgctgtc cagactgtcc gct                                    33
```

<210> SEQ ID NO 24
<211> LENGTH: 21
<212> TYPE: DNA
<213> ORGANISM: Bacillus subtilis

<400> SEQUENCE: 24

```
gcggccgcga tttccaatga g                                                 21
```

<210> SEQ ID NO 25
<211> LENGTH: 21
<212> TYPE: DNA
<213> ORGANISM: Bacillus subtilis

<400> SEQUENCE: 25

```
ggtacctgca tttgccagca c                                                 21
```